US012708358B2

(12) United States Patent
Cortez, Jr. et al.

(10) Patent No.: US 12,708,358 B2
(45) Date of Patent: Aug. 18, 2026

(54) MINIMALLY-INVASIVE DEFECT CLOSURE

(71) Applicant: EDWARDS LIFESCIENCES CORPORATION, Irvine, CA (US)

(72) Inventors: Felino V. Cortez, Jr., Bowie, MD (US); Stephen Cournane, Severn, MD (US); Nancy Ling Chung, Edgewater, MD (US); Luke Anthony Zanetti, Parkton, MD (US); Ashley Nicolette Hinga, Eldersburg, MD (US); Stephen Epstein, Millersville, MD (US)

(73) Assignee: Edwards Lifesciences Corporation, Irvine, CA (US)

( * ) Notice: Subject to any disclaimer, the term of this patent is extended or adjusted under 35 U.S.C. 154(b) by 471 days.

(21) Appl. No.: 18/301,044

(22) Filed: Apr. 14, 2023

(65) Prior Publication Data

US 2024/0341744 A1 Oct. 17, 2024

Related U.S. Application Data

(60) Provisional application No. 63/363,101, filed on Apr. 15, 2022.

(51) Int. Cl.
*A61B 17/04* (2006.01)

(52) U.S. Cl.
CPC .. *A61B 17/0401* (2013.01); *A61B 2017/0409* (2013.01); *A61B 2017/0414* (2013.01); *A61B 2017/0464* (2013.01)

(58) Field of Classification Search
CPC .... A61B 2017/0409; A61B 2017/0414; A61B 2017/00663; A61B 2017/00615; A61B 2017/00575
See application file for complete search history.

(56) References Cited

U.S. PATENT DOCUMENTS 3,131,957 A 5/1964 Musto
3,752,516 A 8/1973 Mumma
4,403,797 A 9/1983 Ragland, Jr.
4,662,376 A 5/1987 Belanger
4,807,625 A 2/1989 Singleton
5,144,961 A 9/1992 Chen et al.
(Continued)

FOREIGN PATENT DOCUMENTS

EP 0791330 A3 11/1997
EP 3505077 A1 7/2019
(Continued)

OTHER PUBLICATIONS

Alfieri, 0. el al., “The double-orifice technique in mitral valve repair: a +A198:A225simple solution for complex problems,” (2001) J. Thorne. Cardiovasc. Surg., 122(4):674-681.
(Continued)

*Primary Examiner* — Alexander J Orkin
(74) *Attorney, Agent, or Firm* — Chang and Hale LLP

(57) ABSTRACT

Septal defect repair involves advancing an elongate shaft into an atrium of a heart of a patient through an outer atrial wall of the heart, contacting an atrial septum of the heart with a distal end of the elongate shaft, deploying a plurality of tissue anchors from the elongate shaft in tissue of the atrial septum, and cinching suture tails associated with the plurality of tissue anchors to at least partially close a defect in the atrial septum.

20 Claims, 19 Drawing Sheets

(56) References Cited

U.S. PATENT DOCUMENTS 5,147,316 A 9/1992 Castillenti
5,312,423 A 5/1994 Rosenbluth et al.
5,391,176 A 2/1995 de la Torre
5,405,352 A 4/1995 Weston
5,454,821 A 10/1995 Harm et al.
5,472,446 A 12/1995 de la Torre
5,507,754 A 4/1996 Green et al.
5,527,323 A 6/1996 Jervis et al.
5,554,184 A 9/1996 Machiraju
5,626,614 A 5/1997 Hart
5,643,293 A 7/1997 Kogasaka et al.
5,681,331 A 10/1997 de la Torre et al.
5,716,368 A 2/1998 de la Torre et al.
5,727,569 A 3/1998 Benetti et al.
5,728,109 A 3/1998 Schulze et al.
5,746,752 A 5/1998 Burkhart
5,769,862 A 6/1998 Kammerer et al.
5,797,928 A 8/1998 Kogasaka
5,824,065 A 10/1998 Gross
5,931,868 A 8/1999 Gross
5,957,936 A 9/1999 Yoon et al.
5,971,447 A 10/1999 Steck, III
6,010,531 A 1/2000 Donlon et al.
6,074,417 A 6/2000 Peredo
6,269,819 B1 8/2001 Oz et al.
6,332,893 B1 12/2001 Mortier et al.
6,562,051 B1 5/2003 Bolduc et al.
6,626,930 B1 9/2003 Allen et al.
6,629,534 B1 10/2003 St. Goar et al.
6,752,810 B1 6/2004 Gao et al.
6,840,246 B2 1/2005 Downing
6,921,408 B2 7/2005 Sauer
6,940,246 B2 9/2005 Mochizuki et al.
6,978,176 B2 12/2005 Lattouf
6,991,635 B2 1/2006 Takamoto et al.
6,997,950 B2 2/2006 Chawla
7,112,207 B2 9/2006 Allen et al.
7,291,168 B2 11/2007 Macoviak et al.
7,294,148 B2 11/2007 McCarthy
7,309,086 B2 12/2007 Carrier
7,316,706 B2 1/2008 Bloom et al.
7,373,207 B2 5/2008 Lattouf
7,431,692 B2 10/2008 Zollinger et al.
7,513,908 B2 4/2009 Lattouf
7,534,260 B2 5/2009 Lattouf
7,608,091 B2 10/2009 Goldfarb et al.
7,618,449 B2 11/2009 Tremulis et al.
7,632,308 B2 12/2009 Loulmet
7,635,386 B1 12/2009 Gammie
7,666,196 B1 2/2010 Miles
7,744,609 B2 6/2010 Allen et al.
7,837,727 B2 11/2010 Goetz et al.
7,871,368 B2 1/2011 Zollinger et al.
7,871,433 B2 1/2011 Lattouf
7,959,650 B2 6/2011 Kaiser et al.
8,029,518 B2 10/2011 Goldfarb et al.
8,029,565 B2 10/2011 Lattouf
8,043,368 B2 10/2011 Crabtree
8,147,542 B2 4/2012 Maisano et al.
8,187,323 B2 5/2012 Mortier et al.
8,226,711 B2 7/2012 Mortier et al.
8,241,304 B2 8/2012 Bachman
8,252,050 B2 8/2012 Maisano et al.
8,292,884 B2 10/2012 Levine et al.
8,303,622 B2 11/2012 Alkhatib
8,333,788 B2 12/2012 Maiorino
8,382,829 B1 2/2013 Call et al.
8,439,969 B2 5/2013 Gillinov et al.
8,454,656 B2 6/2013 Tuval
8,465,500 B2 6/2013 Speziali
8,475,525 B2 7/2013 Maisano et al.
8,500,800 B2 8/2013 Maisano et al.
8,608,758 B2 12/2013 Singhatat et al.
8,663,278 B2 3/2014 Mabuchi et al.
8,771,296 B2 7/2014 Nobles et al.
8,828,053 B2 9/2014 Sengun et al.
8,852,213 B2 10/2014 Gammie et al.
8,888,791 B2 11/2014 Jaramillo et al.
8,940,008 B2 1/2015 Kunis
9,131,884 B2 9/2015 Holmes et al.
9,192,287 B2 11/2015 Saadat et al.
2002/0013571 A1 1/2002 Goldfarb et al.
2003/0023254 A1 1/2003 Chiu
2003/0094180 A1 5/2003 Benetti
2003/0105519 A1 6/2003 Fasol et al.
2003/0120264 A1 6/2003 Lattouf
2003/0120341 A1 6/2003 Shennib et al.
2004/0044365 A1 3/2004 Bachman
2004/0093023 A1 5/2004 Allen et al.
2004/0199183 A1 10/2004 Oz et al.
2005/0004667 A1 1/2005 Swinford et al.
2005/0019735 A1 1/2005 Demas
2005/0075654 A1 4/2005 Kelleher
2005/0119735 A1 6/2005 Spence et al.
2005/0149067 A1 7/2005 Takemoto et al.
2005/0149093 A1 7/2005 Pokorney
2005/0154402 A1 7/2005 Sauer et al.
2005/0216036 A1 9/2005 Nakao
2005/0216077 A1 9/2005 Mathis et al.
2005/0261710 A1 11/2005 Sakamoto et al.
2005/0267493 A1 12/2005 Schreck et al.
2006/0030866 A1 2/2006 Schreck
2006/0100698 A1 5/2006 Lattouf
2006/0111739 A1 5/2006 Staufer et al.
2006/0167541 A1 7/2006 Lattouf
2006/0190030 A1 8/2006 To et al.
2006/0282088 A1 12/2006 Ryan
2007/0001857 A1 1/2007 Hartmann et al.
2007/0005079 A1* 1/2007 Zarbatany .......... A61B 17/0057 606/139
2007/0049952 A1 3/2007 Weiss
2007/0055292 A1 3/2007 Ortiz et al.
2007/0112422 A1 5/2007 Dehdashtian
2007/0112425 A1 5/2007 Schaller et al.
2007/0118151 A1 5/2007 Davidson
2007/0118154 A1 5/2007 Crabtree
2007/0149995 A1 6/2007 Quinn et al.
2007/0197858 A1 8/2007 Goldfarb et al.
2007/0213582 A1 9/2007 Zollinger et al.
2007/0270793 A1 11/2007 Lattouf
2008/0004597 A1 1/2008 Lattouf et al.
2008/0009888 A1 1/2008 Ewers et al.
2008/0065203 A1 3/2008 Khalapyan
2008/0140093 A1 6/2008 Stone et al.
2008/0154286 A1* 6/2008 Abbott ............... A61B 17/0483 606/228
2008/0167714 A1 7/2008 St. Goar et al.
2008/0188893 A1 8/2008 Selvitelli et al.
2008/0195126 A1 8/2008 Solem
2008/0228223 A1 9/2008 Alkhatib
2008/0249504 A1 10/2008 Lattouf et al.
2008/0269781 A1 10/2008 Funamura et al.
2009/0005863 A1 1/2009 Goetz et al.
2009/0012557 A1* 1/2009 Osypka ............. A61B 17/0057 604/93.01
2009/0043153 A1 2/2009 Zollinger et al.
2009/0105729 A1 4/2009 Zentgraf
2009/0105751 A1 4/2009 Zentgraf
2009/0163939 A1* 6/2009 Mabuchi ............ A61B 17/0401 606/228
2009/0259304 A1* 10/2009 O'Beirne .............. A61F 2/2466 606/228
2009/0276038 A1 11/2009 Tremulis et al.
2010/0023056 A1 1/2010 Johansson et al.
2010/0023117 A1 1/2010 Yoganathan et al.
2010/0023118 A1 1/2010 Medlock et al.
2010/0042147 A1 2/2010 Janovsky et al.
2010/0174297 A1 7/2010 Speziali
2010/0179574 A1 7/2010 Longoria et al.
2010/0210899 A1 8/2010 Schankereli
2010/0298930 A1 11/2010 Orlov
2011/0015476 A1 1/2011 Franco
2011/0022083 A1 1/2011 DiMatteo et al.
2011/0022084 A1 1/2011 Sengun et al.

(56) References Cited

U.S. PATENT DOCUMENTS

2011/0028995 A1 2/2011 Miraki et al.
2011/0029071 A1 2/2011 Zlotnick et al.
2011/0060407 A1 3/2011 Ketai et al.
2011/0106106 A1 5/2011 Meier et al.
2011/0144743 A1 6/2011 Lattouf
2011/0264208 A1 10/2011 Duffy et al.
2011/0270278 A1* 11/2011 Overes ............... A61B 17/0487 606/228
2011/0288637 A1 11/2011 De Marchena
2011/0307055 A1 12/2011 Goldfarb et al.
2012/0004669 A1 1/2012 Overes et al.
2012/0143215 A1 6/2012 Corrao et al.
2012/0150223 A1 6/2012 Manos et al.
2012/0179184 A1 7/2012 Orlov
2012/0184971 A1 7/2012 Zentgraf et al.
2012/0203072 A1 8/2012 Lattouf et al.
2012/0226294 A1 9/2012 Tuval
2012/0226349 A1 9/2012 Tuval et al.
2013/0018459 A1 1/2013 Maisano et al.
2013/0035757 A1 2/2013 Zentgraf et al.
2013/0253641 A1 9/2013 Lattouf
2013/0282059 A1 10/2013 Ketai et al.
2013/0345749 A1 12/2013 Sullivan et al.
2014/0031926 A1 1/2014 Kudlik et al.
2014/0039607 A1 2/2014 Kovach
2014/0067052 A1 3/2014 Chau et al.
2014/0114404 A1 4/2014 Gammie et al.
2014/0214152 A1 7/2014 Bielefeld
2014/0243968 A1 8/2014 Padala
2014/0364938 A1 12/2014 Longoria et al.
2015/0032127 A1 1/2015 Gammie et al.
2015/0045879 A1 2/2015 Longoria et al.
2017/0325794 A1* 11/2017 Willard .............. A61B 17/1227
2019/0000624 A1* 1/2019 Wilson .................. A61F 2/2466
2019/0029672 A1* 1/2019 Nobles ............... A61B 17/0491
2019/0175346 A1 6/2019 Schaffner et al.
2020/0155315 A1 5/2020 Zhang et al.
2020/0214694 A1* 7/2020 Nobles ............... A61B 17/0482
2021/0321996 A1* 10/2021 Dharan .................... A61B 8/12
2021/0369266 A1* 12/2021 Lau .................... A61B 17/0482
2023/0149005 A1* 5/2023 Agnihotri .......... A61B 17/0057 606/153
2023/0210520 A1* 7/2023 Dale .................. A61B 17/0469 606/139
2024/0090942 A1* 3/2024 Lau .................... A61B 18/1492

FOREIGN PATENT DOCUMENTS

JP 2013517110 A 5/2013
WO 2004037463 A1 5/2004
WO 2006127509 A2 11/2006
WO 2007100268 A2 9/2007
WO 2007119057 A1 10/2007
WO 2008013869 A2 1/2008
WO 2008124110 A3 12/2008
WO 2008143740 A3 2/2009
WO 2006078694 A3 4/2009
WO 2009081396 A2 7/2009
WO 2010070649 A1 6/2010
WO 2010105046 A1 9/2010
WO 2012137208 A1 10/2012
WO 2013003228 A1 1/2013
WO 2014093861 A1 6/2014
WO 2015020816 A1 2/2015
WO 2016192481 A1 12/2016

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in honheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitra! valve repair by replacement of chordae tendineae with polytetrafluoroethylene sutures," ( 1991) J. Thorne. Cardiovasc. Surg., 101 (3 ): 495-50 I.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heal1 Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for detenning proper length of al1ificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "Ring plus String: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal Tim Ore*, Case No. JPR2016-00208, Decision on Institution of Inter Faries Review, 37 CFR §42. I 08, Paper 6, Entered May 24, 2016, 28 pages.

*Neochord, Inc.* v. *University of Maryland, Baltimore*, Case No. IPR2016-00208, Declaration of Dr. Lishan Aklog, dated Nov. 17, 2015, 91 pages.

*Neochord, Inc.* v. *University of Maryland, Baltimore*, Case No. IPR2016-00208, Petition for inter ParlesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127(2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al.—Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

(56) References Cited

OTHER PUBLICATIONS

Sarsam, M.A. I., "Simplified technique for determining the length of artificial cl1ordae in milral valve repair," (2002) Ann. Thorac. Surg., 73(5): 1659-1660.
Savage, E. B. et al., Use of mitral valve repair: analysis of contemporary United States experience reported to the society of thoracic surgeons national cardiac database, . . . (2003) Ann. Thorne. Surg., 75:820-825.
Speziali, G. et al., "Coll'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.
Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.
Von Oppell, U. 0. et al., "Chordal replacement for both minimally invasive and conventional mitral valve surgery using promcasurcd Gore-Tex loops," (2000) Ann. Thorne. Surg., 70(6):2166-2168.
Zussa, C. et al., Artificial mitral valve chordae: experimental and clinical experience;- ( 1990) Ann. Thorne. Surg., 50(3):367-373.
Zussa, C. et al., "Seven-year experience with chordal replacement with expanded polytetrafluoroethylene in floppymitral valve," (1994)1. Thorac. Cardiovasc. Surg., 108(1):37-41.
Zussa, C. et al., "Surgical technique for artificial mitral chordae implantation," ( 1991) Journal of Cardiac Surgery, 6(4):432-438.
Zussa, C., "Artificial chordae," (1995) J. Heart Valve Dis., 4(2):S249-S256.

* cited by examiner 114
110
100
150
145
140
120
195

1
60
16
100
210
18
221
2
220
222
200
3
110

DISTAL
PROXIMAL
100
200
110
1
2
3
4
5
6
8
110
114
182
181
95a
16
18
90a
90b
95b
19
29

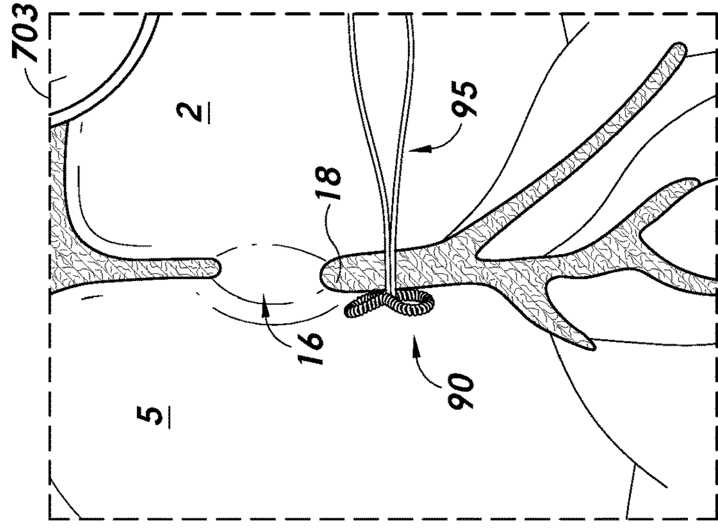
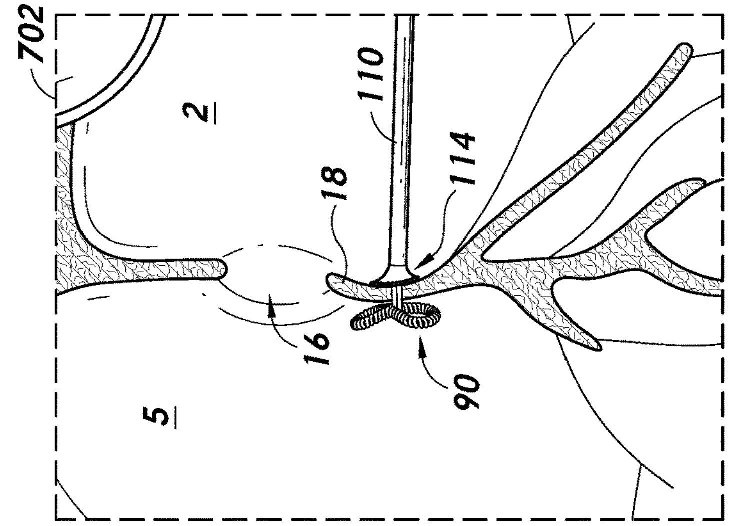
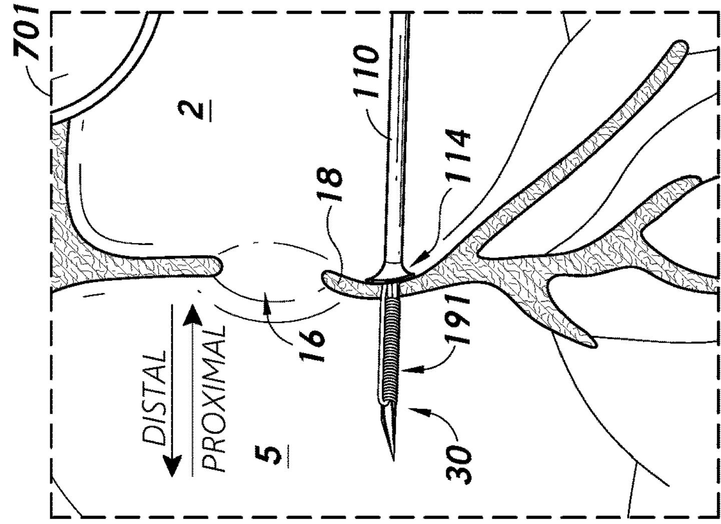
FIG. 7-1

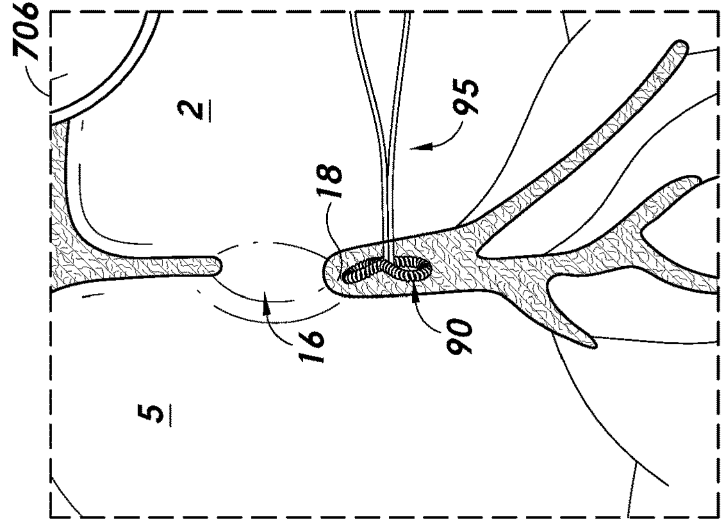
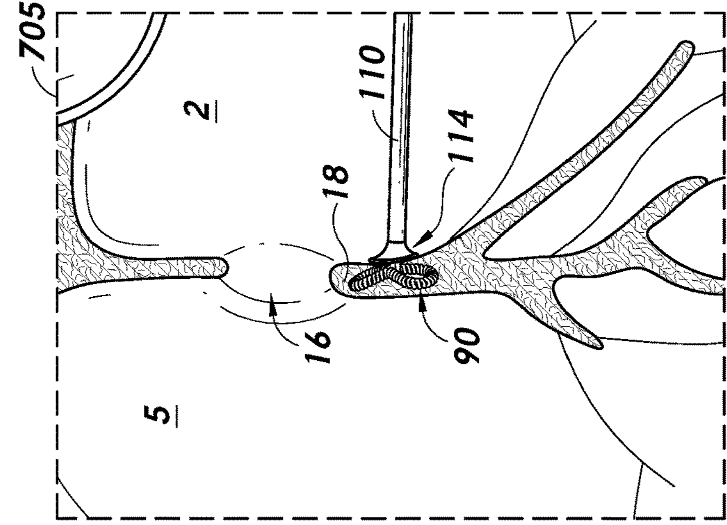
FIG. 7-2
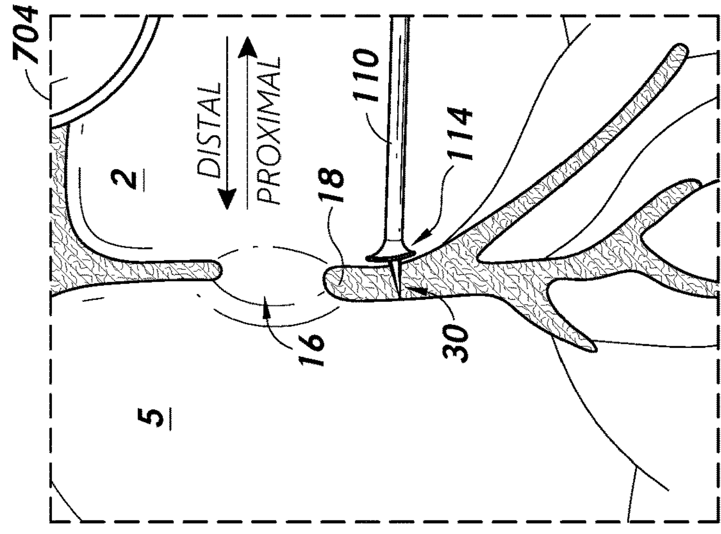

100
200
DISTAL
PROXIMAL
110
1201
141
138
137
95
110
137
80
2
95a
95b
16
90b
90a
18
5

MINIMALLY-INVASIVE DEFECT CLOSURE

RELATED APPLICATION

This application claims the benefit of U.S. Patent Application No. 63/363,101, filed on Apr. 15, 2022, the entire disclosure which is incorporated by reference.

BACKGROUND

The present disclosure generally relates to the field of medical procedures and devices. Openings and/or other defects can form or otherwise be present in certain biological tissue walls, such as cardiac septa. Such defects can negatively impact physiological function and/or health in some patients and cases.

SUMMARY

Described herein systems, methods, and devices to facilitate the treatment of defects in biological tissue, including inventive minimally-invasive septal defect closure procedures and associated delivery systems/devices, and procedures for delivering and deploying the same.

For purposes of summarizing the disclosure, certain aspects, advantages and novel features have been described. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of the inventions. In addition, various features of different disclosed examples can be combined to form additional examples, which are part of this disclosure. Throughout the drawings, reference numbers may be reused to indicate correspondence between reference elements.

FIGS. 7-1 and 7-2 show tissue anchors deployed on and within a tissue wall, respectively, in accordance with one or more examples.

FIGS. 10-1 and 10-2 show an occluder patch secured over a septal defect in accordance with one or more examples.

FIGS. 11-1 and 11-2 show a suture-secured occluder patch implanted over a septal defect in accordance with one or more examples.

FIGS. 15-1, 15-2, and 15-3 provide a flow diagram illustrating a process for repairing a septal defect using a multi-needle repair device in accordance with one or more examples.

FIGS. 16-1, 16-2, and 16-3 provide images of cardiac anatomy and certain devices/systems corresponding to operations of the process of FIGS. 15-1, 15-2, and 15-3 in accordance with one or more examples.

FIGS. 17-1 through 17-5 show tissue anchors that can be used for defect closure in accordance with one or more examples.

DETAILED DESCRIPTION

Figure 1:
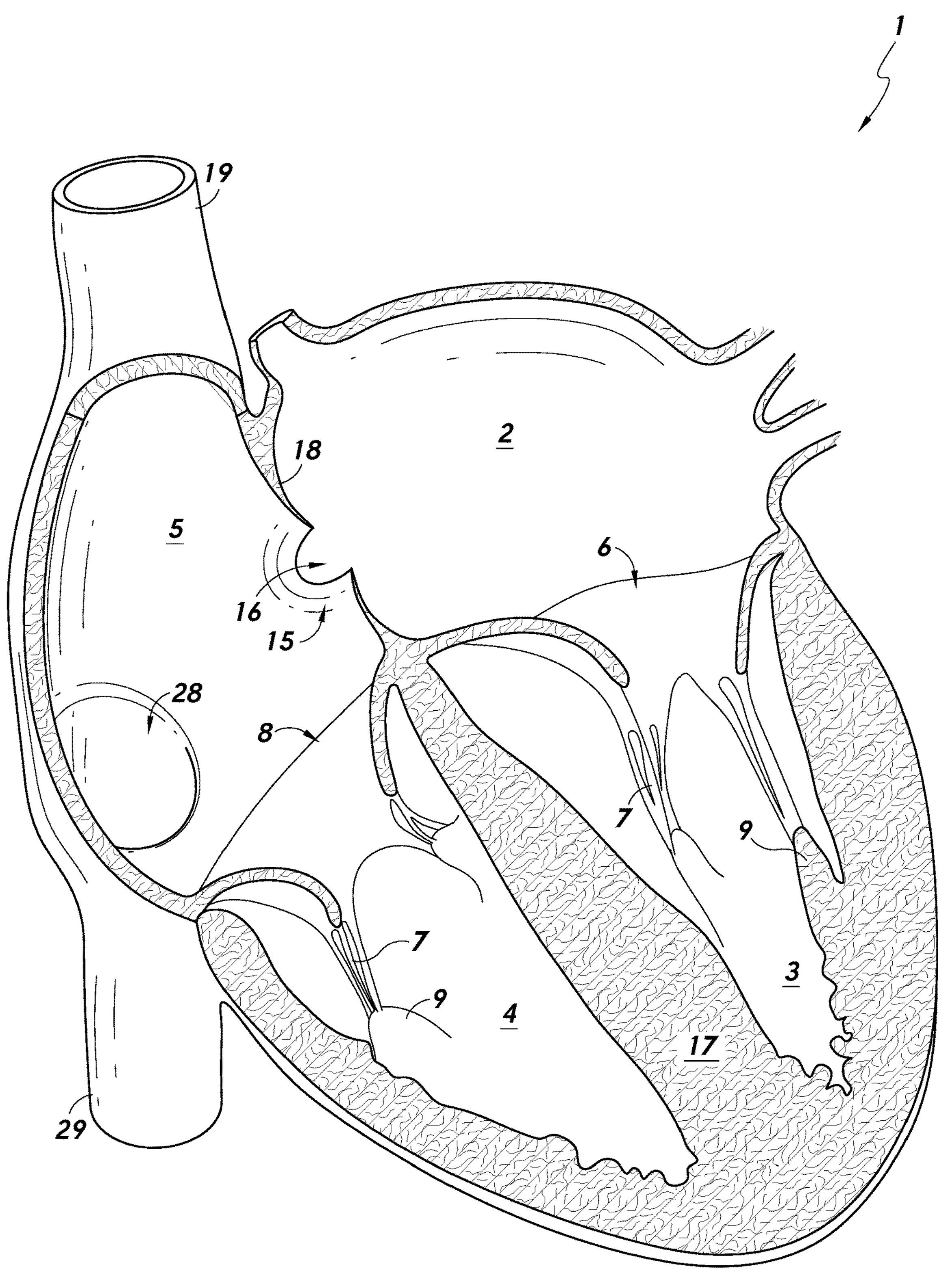
FIG. 1 illustrates an example representation of a human heart in accordance with one or more examples.

The headings provided herein are for convenience only and do not necessarily affect the scope or meaning of the claimed invention.

Although certain preferred examples are disclosed below, inventive subject matter extends beyond the specifically disclosed examples to other alternative examples and/or uses and to modifications and equivalents thereof. Thus, the scope of the claims that may arise herefrom is not limited by any of the particular examples described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain examples; however, the order of description should not be construed to imply that these operations are order dependent. Additionally, the structures, systems, and/or devices described herein may be embodied as integrated components or as separate components. For purposes of comparing various examples, certain aspects and advantages of these examples are described. Not necessarily all such aspects or advantages are achieved by any particular example. Thus, for example, various examples may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that may be similar in one or more respects. However, with respect to any of the examples disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

Where an alphanumeric reference identifier is used that comprises a numeric portion and an alphabetic portion (e.g., '10a,' '10' is the numeric portion and 'a' is the alphabetic portion), references in the written description to only the numeric portion (e.g., '10') may refer to any feature identified in the figures using such numeric portion (e.g., '10a,' '10b,' '10c,' etc.), even where such features are identified with reference identifiers that concatenate the numeric portion thereof with one or more alphabetic characters (e.g., 'a,' 'b,' 'c,' etc.). That is, a reference in the present written description to a feature '10' may be understood to refer to either an identified feature '10a' in a particular figure of the present disclosure or to an identifier '10' or '10b' in the same figure or another figure, as an example.

Certain standard anatomical terms of location are used herein to refer to certain device components/features and to the anatomy of animals, and namely humans, with respect to the preferred examples. Although certain spatially relative terms, such as "outer," "inner," "upper," "lower," "below," "above," "vertical," "horizontal," "top," "bottom," "under," "over," "topside," "underside," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

The present disclosure relates to systems, devices, and methods for at least partially closing a defect/opening in a tissue wall, such as an atrial or ventricular septum. Such procedures may advantageously be minimally-invasive, such that they can be performed on a beating heart without the need for cardiac bypass. Solutions presented herein provide for implantation/deployment of a plurality of tissue anchors in areas adjacent to and/or around an opening/defect in a tissue wall, such as an atrial septal defect, wherein such tissue anchors may be cinched/pulled together in some manner as to cause the edges of the opening/defect to be brought together, thereby potentially reducing the shunt flow therethrough. For example, suture tails coupled to, or otherwise associated with, tissue anchors implanted in an atrial septal wall may be cinched together to close an atrial septal defect and tied/secured on an opposite side of the septal wall from the tissue anchors to hold the septal defect at least partially closed.

In some implementations, examples of the present disclosure involve the utilization of a delivery device/system having an elongate shaft configured to allow for advancement and deployment therethrough/therefrom of tissue anchors that may be implanted in and/or through the septal wall. The delivery device may further be configured to facilitate securing of the tissue anchors and/or associated suture tails together to thereby bring tissue areas around the periphery of the septal defect/opening together and reduce or eliminate the shunt opening in the tissue wall. When the delivery device has been used to successfully deploy the desired number of tissue anchors around the septal defect, the suture tails or other cords/lines associated with the tissue anchors may be cinched with a suitable lock or fastener, such as a suture-locking knot as described in greater detail below. Such cinching may advantageously bring the edges of the tissue toward the center of the defect and/or in a manner as to approximate edges of the opening associated with the tissue anchor implantation locations to thereby reduce shunt flow.

In some examples, tissue anchors employed for septal defect closure may comprise tissue anchor forms formed of suture(s), such as coiled suture forms, which may be manipulated (e.g., pulled-on) to form a bulky knot form. Such suture-type tissue anchors may be preferable over other metallic, plastic or other rigid anchor options. For example, metal or plastic tissue anchors may be prone to cause tissue irritation and/or obstruction/interference with blood flow in the area of one or more heart valves, such as the pulmonary valve or aortic valve. Furthermore, such tissue anchors may present a risk of dislodgment or disconnection in a manner as to release the components into the circulation, which can cause embolization risk and/or cause the treated defect to reopen. Suture-type tissue anchors as disclosed in connection with examples of the present disclosure, in some examples, can be formed of the same line(s) of suture forming the suture tail(s) associated with the tissue anchor, thereby providing a reduced risk of detachment of the tissue anchor from the corresponding suture tail.

Cardiac Physiology

The anatomy of the heart is described below to assist in the understanding of certain inventive concepts disclosed herein. In humans and other vertebrate animals, the heart generally comprises a muscular organ having four pumping chambers, wherein the flow between chambers and vessels associated therewith is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aortic, etc.).

FIG. 1 illustrates a vertical/frontal cross-sectional view of an example heart 1 having various features/anatomy relevant to certain aspects of the present inventive disclosure. The heart 1 includes four chambers, namely the left atrium 2, the left ventricle 3, the right ventricle 4, and the right atrium 5. In terms of blood flow, blood generally flows from the right ventricle 4 into the pulmonary artery (not shown in FIG. 1 for visual clarity) via the pulmonary valve (not shown in FIG. 1 for visual clarity), which separates the right ventricle 4 from the pulmonary artery and is configured to open during systole so that blood may be pumped toward the lungs and close during diastole to prevent blood from leaking back into the heart from the pulmonary artery. The pulmonary artery carries deoxygenated blood from the right side of the heart to the lungs.

In addition to the pulmonary valve, the heart 1 includes three additional valves for aiding the circulation of blood therein, including the tricuspid valve 8, the aortic valve (not shown in FIG. 1 for visual clarity), and the mitral valve 6. The tricuspid valve 8 separates the right atrium 5 from the right ventricle 4. The tricuspid valve 8 generally has three cusps or leaflets and may generally close during ventricular contraction (e.g., systole) and open during ventricular expansion (e.g., diastole). The mitral valve 6 generally has two cusps/leaflets and separates the left atrium 2 from the left ventricle 3. The mitral valve 6 is configured to open during diastole so that blood in the left atrium 2 can flow into the left ventricle 3, and, when functioning properly, closes during systole to prevent blood from leaking back into the left atrium 2. The aortic valve separates the left ventricle 3 from the aorta (not shown in FIG. 1 for visual clarity). The aortic valve is configured to open during systole to allow blood leaving the left ventricle 3 to enter the aorta, and close during diastole to prevent blood from leaking back into the left ventricle 3.

The heart valves may generally comprise a relatively dense fibrous ring, referred to as the annulus, as well as a plurality of leaflets or cusps attached to the annulus. Generally, the size of the leaflets/cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. Disfunction of a heart valve and/or associated leaflets (e.g., pulmonary valve disfunction) can result in valve leakage and/or other health complications.

The atrioventricular (e.g., mitral and tricuspid) heart valves may further comprise a collection of chordae tendineae 7 and papillary muscles 9 for securing the leaflets of the respective valves to promote and/or facilitate proper coaptation of the valve leaflets and prevent prolapse thereof. The papillary muscles 9, for example, may generally comprise finger-like projections from the ventricle wall. The valve leaflets are connected to the papillary muscles by the chordae tendineae 7.

A wall of muscle, referred to as the septum, separates the left-side chambers from the right-side chambers. In particular, an atrial septum wall portion 18 (referred to herein as the "atrial septum," "interatrial septum," or "septum") separates the left atrium 2 from the right atrium 5, whereas a ventricular septum wall portion 17 (referred to herein as the "ventricular septum," "interventricular septum," or "septum") separates the left ventricle 3 from the right ventricle 4. The atrial septum 18 is generally a relatively thin wall tissue, whereas the ventricular septum 17 is typically thicker than they atrial septum 18.

A septal defect or orifice (e.g., atrial septal defect 16) can form in a septal wall in the form of a perforation, aperture, or other hole or passage through the tissue wall. A septal defect can occur congenitally or by puncturing the septum with a medical device to access a location (e.g., left atrium 2) within the heart. While some septal defects can be relatively benign and have relatively little impact on a patient's health, other septal defects can be more serious. Septal defects can result in left-to-right shunting of blood, wherein oxygen-rich blood is shunted to the relatively oxygen-depleted right-side chamber(s) (e.g., right atrium 5). In some cases, such shunting can cause volume overload in the right side of the heart and/or insufficient oxygenated blood being delivered to the body. In some cases, a thrombus or other embolus can travel from the right to the left, potentially causing various health complications, such as migraines and/or stroke.

Atrial septal defects represent a commonly recognized congenital cardiac anomaly that can present in adulthood. Atrial septal defects can be characterized by a defect/opening in the interatrial septum 18 allowing pulmonary venous return from the left atrium 2 to pass directly to the right atrium 5. Depending on the size of the defect, this can result in a spectrum of diseases, including cardiac sequelae, right-sided volume overload, pulmonary arterial hypertension, arrhythmias, and/or other complications. Patients who have relatively large defects/shunts may experience symptoms related to excess pulmonary blood flow and/or right-sided heart failure, such as heart murmur, palpitations, fatigue and exercise intolerance, cyanosis, peripheral edema, and others.

In some instances, an atrial defect is formed in the area of the fossa ovalis 15, which is a depression in the right atrium 5 of the heart, at the level of the interatrial septum 18. For example, one type of septal defect is a patent foramen ovale (PFO), which is an opening in the area of the fossa ovalis 15. Because the fetal lungs do not provide air prior to birth, fetal blood is oxygenated by the mother in utero via the umbilical cord and placenta. To provide for circulation of such oxygenated blood, the fetal blood circulation system includes certain vessels and openings that are open during fetal development but typically close soon after birth. One such opening is the foramen ovale, a central location in the interatrial septum where the septum primum and the septum secundum overlap, which permits blood to flow from the right atrium into the left atrium in a fetal heart, thereby allowing blood to bypass the fetal lungs and flow directly from the venous circulation to the arterial circulation. After birth, the infant's lungs typically provide oxygenation to the blood, and it is generally undesirable to continue having blood shunt/flow from the venous circulation to the arterial circulation without first passing through the lungs. At birth, left atrial pressure increases as the pulmonary circulation is established. This pressure increase typically causes the closure of a flap of tissue which occludes the foramen ovale and then heals/fixes in the occluded position shortly after birth. The foramen ovale becomes the fossa ovalis depression as the foramen closes.

In some individuals, however, the tissue flap does not heal to permanently occlude the foreman ovale. This condition is known as a patent (e.g., open) foramen ovale (PFO). While a PFO can be a relatively benign condition in some cases, PFOs can lead to migraines and other conditions in some individuals. In some cases, a PFO can cause a stroke by permitting blood containing small thrombi/embolus to bypass the lungs (which would otherwise filter out such small thrombi) and flow directly from the venous circulation to the arterial circulation and ultimately into the brain.

In addition to patent formen ovale, septal defects can be caused in connection with certain medical interventions. For example, the atrial septum can serve as an access point for certain catheterization procedures for accessing the left atrium from the venous system (e.g., right atrium and inferior or superior vena cava). For example, the atrial septum can serve as a point of percutaneous access for atrial fibrillation therapy, left atrial appendage closure, percutaneous mitral valve repair, and percutaneous mitral valve replacement. In such procedures, devices may traverse across the atrial septum and, by doing so, may leave a defect/opening in the atrial septum that does not close spontaneously.

Health Conditions and Treatments Associated with Septal Defects

As referenced above, defects in cardiac tissue walls, such as patent foramen ovale or other septal defects, can adversely affect the health of an individual. For example, atrial septal defects can cause ischemic stroke due to embolism of venous emboli passing to the arterial circulation from thrombus traversing a patent foramen ovale. In addition, patent foramen ovale can cause migraine headaches in some individuals.

Treatments for patent foramen ovale (PFO) and other septal defects can include open-heart surgery, as well as percutaneous (e.g., transcatheter) procedures. Open-heart surgery for septal defect closure can involve suturing the opening/defect closed. Such open-heart surgical treatment can be associated with a variety of risks typically associated with cardiac surgery. Percutaneous methods can involve deploying mesh, clamshell, plug, or other similar implanted devices to close the opening. Other treatments can include using heat, laser, RF, or other energy to treat the tissue of (or adjacent to) the septal defect to induce the tissue to permanently close the opening. Such percutaneous methods can be complicated and/or involve relatively large implant devices or uncertain tissue treatments. In some cases, the implantation of a septal defect closure device forecloses the ability to re-cross the septum in connection with a subsequent intervention.

Minimally-Invasive Defect Closure

As referenced above, various surgical, open-chest procedures may be implemented to close a septal defect. However, some such solutions present various issues that are not present and/or have a lesser impact with respect to solutions embodied in the examples of the present disclosure. For example, some septal defect occlusion implants may include bulky structure/forms in either or both of the left and right atria that can interfere with aortic and/or tricuspid valve function. In addition, with respect to occluder solutions including metal frames, use of such metal frames can present risk of fatigue-related failure. Suture-based tissue anchors and cinching lines in accordance with aspects of the present disclosure can advantageously resist fatigue over a substantial postoperative period.

Some septal defect occluder solutions may not be configured to fully conform to the septal defect hole/opening and/or the topology/anatomy associated with the septum and/or the defect. Examples of the present disclosure advantageously can be implemented to specifically target the anatomy around a particular septal defect and produce a substantially customized closure/implant solution.

Some solutions for closing septal defects are associated with relatively complex implantation procedures and devices that may suffer from limited maneuverability/articulation capability inside the heart chamber during placement, which can increase risks associated with such procedures and/or reduce efficacy of the procedure(s). Using direct minimally-invasive transatrial access in accordance with aspects of the present disclosure can provide a relatively simplified and accurate access to the atrial septum (or other target tissue wall) for a repair procedure.

Figure 2:
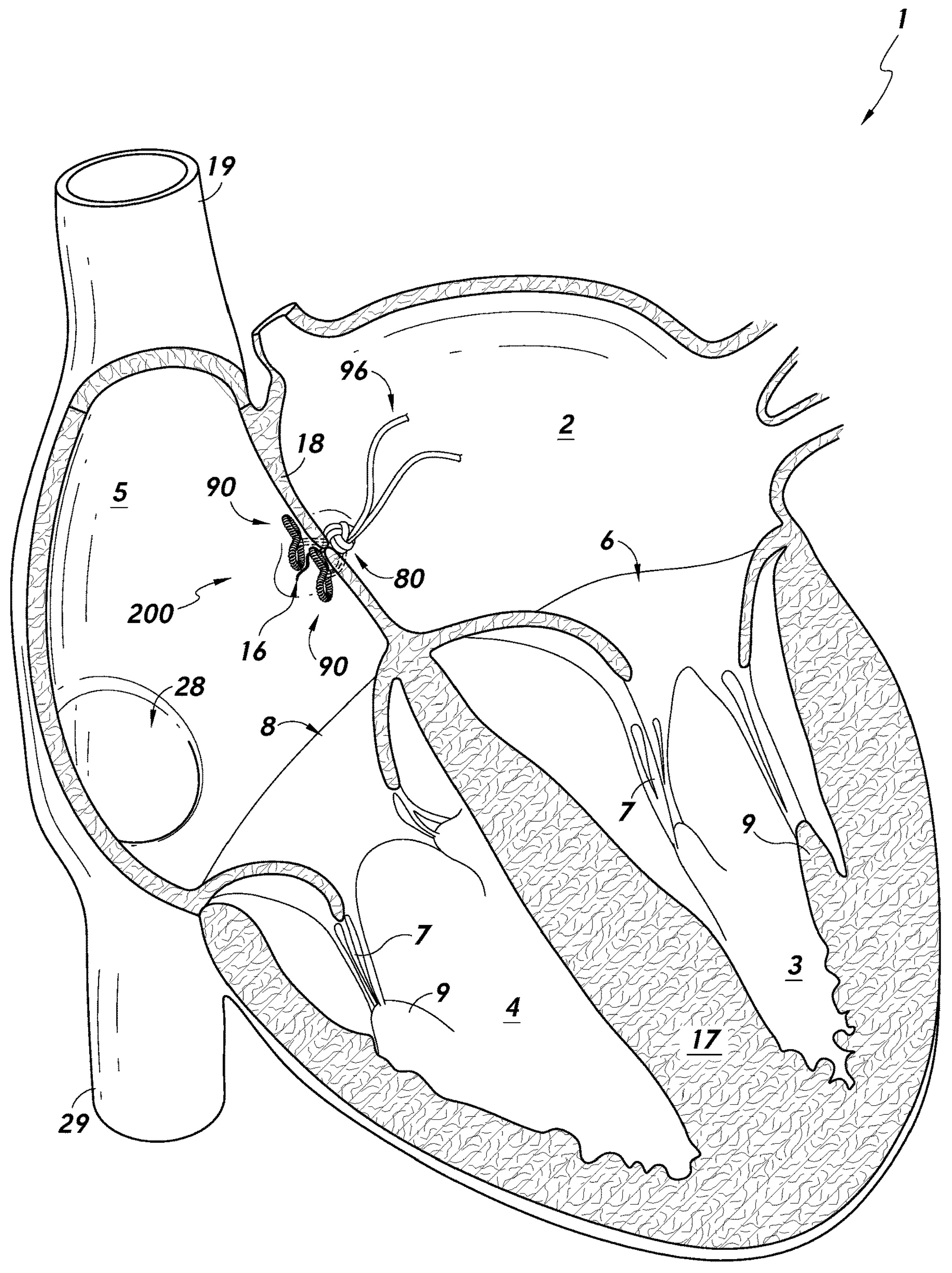
FIG. 2 illustrates a septal defect that has been closed using minimally-invasive, suture- and/or tissue-anchor-based closure processes and/or devices/systems in accordance with one or more examples.

FIG. 2 illustrates a septal defect 16 that has been closed using minimally-invasive, suture- and/or tissue-anchor-based closure processes and/or devices/systems in accordance with one or more examples. The defect-closure implant 200 includes a plurality of tissue anchors 90 implanted/deployed around the defect 16 and pulled/cinched together by suture tails 96 emanating therefrom, wherein the suture tails 96 are locked/secured in the cinched configuration by a suture fastener/lock 80. The lock 80 can comprise a specialized suture-form knot or other lock/fastener that is configured to hold tension in the suture tails 96 of two or more tissue anchors without slippage of such sutures. Alternatively, any type of clip, clamp, or non-suture-type lock/fastener may be utilized to hold the tension in the suture tails 96 and/or prevent the tissue anchors 90 from migrating away from one another. The suture tails 96 may be longer lengths of line that are cut-off intraoperatively; FIG. 2 shows the suture tails 96 in a cut-off state, where smaller suture tail remnants remain, which may be of any length.

Examples of septal defect closure devices, systems, and methods disclosed herein may employ certain tissue anchor delivery devices/systems, which may be configured to allow a surgeon to access the internal anatomy (e.g., interatrial septum) of the patient and execute certain anchoring steps/actions, wherein such anchors may be used to draw edges of a defect/opening in a tissue wall together to occlude/close such opening. Any suitable or desirable tissue anchor delivery device/system may be implemented in connection with examples of the present disclosure, some examples of which are illustrated and described in the present disclosure. For example, it is contemplated that any of the various delivery devices disclosed in U.S. Pat. Nos. 7,635,386, 8,852,213, 10,765,515, 10,864,080 and 11,065,120; and PCT Application No. PCT/US2012/043761 (published as WO 2013/003228) and PCT Application No. PCT/US2016/055170 (published as WO 2017/059426), the contents of which are hereby explicitly incorporated by reference in their entireties for all purposes, may be implemented in accordance with examples of the present disclosure.

In some implementations, defect closure processes in accordance with aspects of the present disclosure may be implemented using a delivery device/system comprising a handle, an actuator operably coupled to the handle, a pusher component/device, a needle, and/or a distal anchor coupled with the tether, which may be disposed and/or an advanced within an elongate shaft (e.g., rigid shaft) projecting from the delivery device/system. The tissue anchor implemented may be composed of suture material, which may be designed/configured to be formed into a bulky knot configuration. Such knot/anchor may comprise polytetrafluoroethylene (e.g. PTFE), or other suture material suitable for cardiac surgery. In some examples, other types of mechanical fasteners may be implemented as tissue anchors. It is contemplated that suture-type bulky knot anchors may be implemented in connection with defect repair procedures and devices/systems of the present disclosure, some examples of which are illustrated and described in the present disclosure. For example, it is contemplated that any of the various tissue anchors disclosed in U.S. Publication No. 2019/0000624 and U.S. Pat. Nos. 7,635,386, 8,852,213, 10,765,515, and 11,065,120, the contents of which are hereby explicitly incorporated by reference in their entireties for a purposes, may be implemented in accordance with examples of the present disclosure.

The particular delivery device/system utilized may be inserted into the left or right atrium through a valved introducer, which may provide access to the atrial septum. Such access may the implemented in combined utilization with transesophageal echocardiogram guidance or intracardiac echocardiogram guidance to guide/track the movement and proper positioning of the device/system for tissue anchor deployment.

Figure 3:
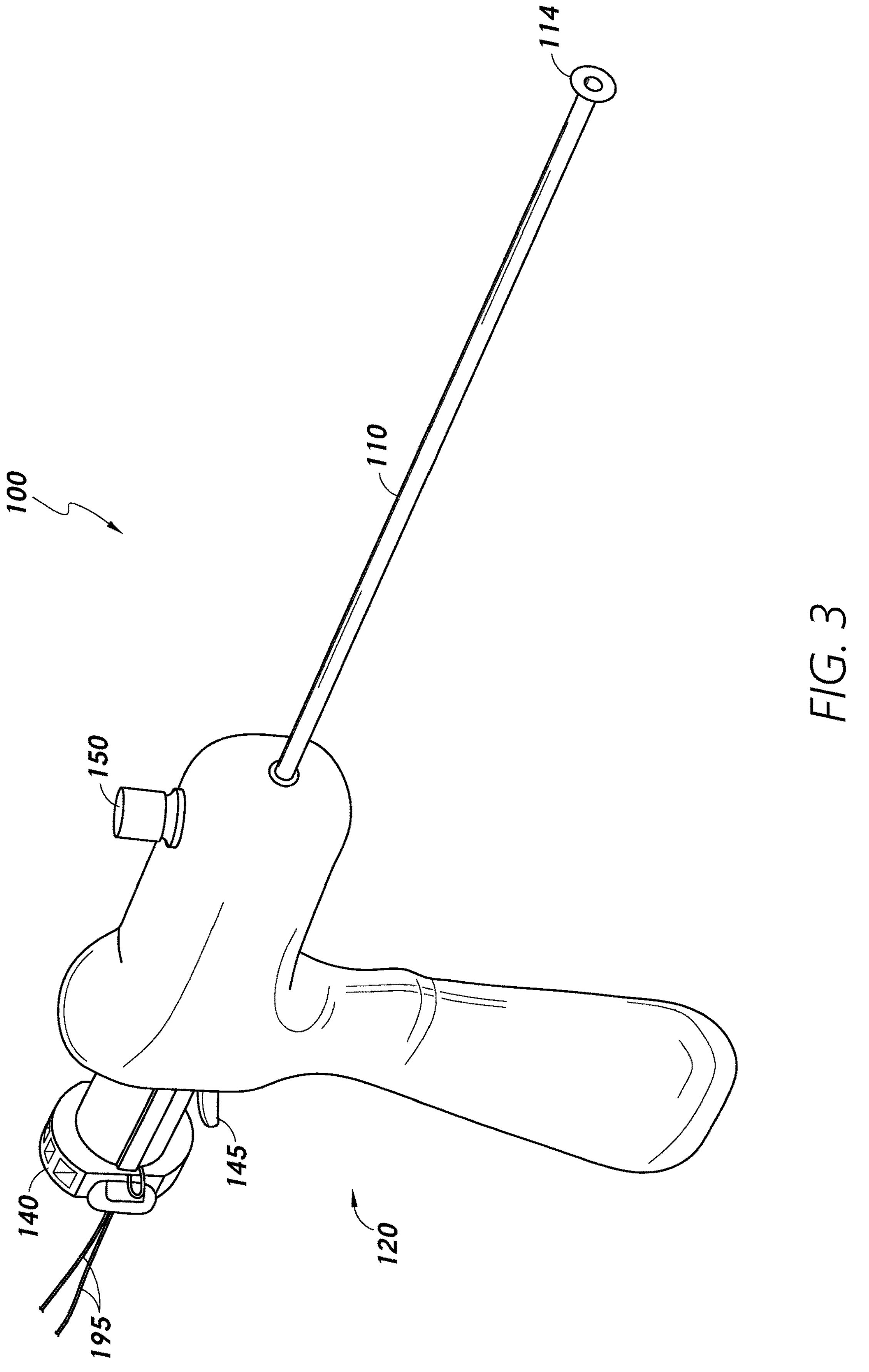
FIG. 3 is a perspective view of a defect repair system/device in accordance with one or more examples.

FIG. 3 is a perspective view of a defect repair device 100 in accordance with one or more examples. For convenience, the defect repair device/system 100 is described in some contexts below as a tissue anchor delivery device or system. The tissue anchor delivery system 100 may be used to repair/close a defect/opening in a septal wall of a heart, or other tissue wall. For example, the tissue anchor delivery system 100 may be used to reduce the degree of atrial shunting in patients suffering from a septal defect. In order to repair such a defect, the tissue anchor delivery system 100 may be utilized to deliver and anchor tissue anchors, such as suture-knot-type tissue anchors, in a septal wall around a defect/hole in the septal wall. As described in detail below, such procedure may be implemented on a beating heart.

The delivery system 100 includes a rigid elongate tube/shaft 110 forming at least one internal working lumen. Although described in certain examples and/or contexts as comprising a rigid elongate tube or shaft, it should be understood that tubes, shafts, lumens, conduits, and the like disclosed herein may be either rigid, at least partially rigid, flexible, and/or at least partially flexible. Therefore, any such component described herein, whether or not referred to as rigid herein should be interpreted as possibly being at least partially flexible. In accordance with the present disclosure, the rigid elongate tube 110 may be referred to as a shaft for simplicity. Implementation of a defect-repair procedure utilizing the delivery system 100 can be performed in conjunction with certain imaging technology designed to provide visibility of the shaft 110 of the delivery system 100 according to a certain imaging modality, such as echo imaging. Generally, when performing a defect-repair procedure utilizing the tissue anchor delivery system 100, the operating physician may advantageously work in concert with an imaging technician, who may coordinate with the physician to facilitate successful execution of the valve-repair procedure.

In addition to the delivery shaft 110, the delivery system 100 may include a plunger feature 140, which may be used or actuated to manually deploy a pre-formed knot, such as a bulky knot as described in detail below. In some examples, the actuator 140 is a trigger-type actuator. The tissue anchor delivery system 100 may further include a plunger lock mechanism 145, which may serve as a safety lock that locks the valve delivery system until ready for use or deployment of a leaflet anchor as described herein. The plunger 140 may have associated therewith a suture-release mechanism, which may be configured to lock in relative position a pair of suture tails 195 associated with a pre-formed knot anchor (not shown) to be deployed. For example, the suture portions 195 may be ePTFE sutures. The system 100 may further comprise a flush port 150, which may be used to de-air the lumen of the shaft 110. For example, heparinized saline flush, or the like, may be connected to the flush port 150 using a female Luer fitting to de-air the defect-repair system 100. The term "lumen" is used herein according to its broad and ordinary meaning, and may refer to a physical structure forming a cavity, void, pathway, or other channel, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the term "lumen" may refer to the elongate tubular structure and/or to the channel or space within the elongate tubular structure.

The lumen of the shaft 110 may house one or more needles (not shown) that is/are wrapped at least in part with a pre-formed knot suture-form anchor, as described in detail herein. In some examples, the shaft 110 presents a relatively low profile. For example, the shaft 110 may have a diameter of approximately 3 mm or less (e.g., about 9 Fr). The shaft 110 is associated with an atraumatic tip 114 feature. The atraumatic tip 114 can be an echogenic tissue-contact component, which may be used for deployment and/or positioning of the suture-type tissue anchors. The atraumatic tip 114, disposed at the distal end of the shaft 110, may be configured to have deployed therefrom a wrapped pre-formed suture knot (e.g., suture-form), as described herein.

The atraumatic tip 114 may be referred to as an "end effector." In addition to one or more pre-formed knot suture-forms and associated needles, the shaft 110 may house an elongated knot pusher tube (not shown; also referred to herein as a "pusher"), which may be actuated using the actuator/plunger 140 in some examples. As described in further detail below, the tip 114 provides a surface against which the target septal/tissue wall may be held in connection with deployment of a tissue anchor.

The delivery device 100 may be used to deliver a "bulky knot" type tissue anchor, as described in greater detail below. For example, the delivery device 100 may be utilized to deliver a tissue anchor (e.g., bulky knot) on a distal side of a septal wall (e.g., right atrial side when approach/access is from the left atrium, or vice versa). The tip 114 (e.g., end effector), can be placed in contact with, for example, the left atrial side of an interatrial septum.

The tip 114 can be coupled to the distal end portion of the shaft 110, wherein the proximal end portion of the shaft 110 may be coupled to a handle portion 120 of the delivery device 100, as shown. Generally, the elongate pusher (not shown) may be movably disposed within a lumen of the shaft 110 and coupled to a pusher hub (not shown) that is movably disposed within the handle 120 and releasably coupled to the actuator/plunger 140. One or more needles (not shown) carrying one or more pre-formed tissue anchor suture-forms can be movably disposed within one or more lumens of the pusher and coupled to a needle hub (not shown) that is also coupled to the actuator/plunger 140. The plunger 140 can be used to actuate or move the needle and the pusher during deployment of a tissue anchor (see, e.g., FIGS. 7-1 and 7-2) and is movably disposed at least partially within the handle 120. For example, the handle 120 may define a lumen in which the plunger 140 can be moved. During operation, the pusher may also move within the lumen of the handle 120. The plunger lock 145 can be used to prevent the plunger 140 from moving within the handle 120 during storage and prior to performing a procedure to deploy a tissue anchor.

The needle(s) may have the pre-formed knot(s) disposed about a distal portion thereof while maintained in the shaft 110. For example, the pre-formed knot(s) may be formed of one or more sutures configured in a coiled suture-form (see image 701 of FIG. 7-1) having a plurality of winds/turns around the needle over a portion of the needle that is associated with a longitudinal slot in the needle that runs from the distal end thereof. Although the term "suture-form" is used herein, it should be understood that such components/forms may comprise suture, wire, or any other elongate material wrapped or formed in a desired configuration. The coiled suture-form can be provided or shipped disposed around the needle. In some instances, two suture tails extend from each coiled suture-form. The suture tails 195 may extend through the lumen of the particular needle and/or through a passageway of the plunger 140 and may exit the plunger 140 at a proximal end portion thereof. The coiled suture-form may advantageously be configured to be formed into a suture-type tissue anchor (referred to herein as a "bulky knot") in connection with an anchor-deployment procedure, as described in more detail below. The coiled suture-form can be configurable to a knot/deployed configuration by approximating opposite ends of the coiled portion thereof towards each other to form one or more loops.

The repair device/system 100 can further include a suture/tether catch mechanism (not shown) coupled to the plunger 140 at a proximal end of the delivery device 100, which may be configured to releasably hold or secure a suture 195 extending through the delivery device 100 during delivery of a tissue anchor as described herein. The suture catch can be used to hold the suture 195 with a friction fit or with a clamping force and can have a lock that can be released after the tissue anchor has been deployed/formed into a bulky knot, as described herein. As described herein, the anchor delivery device 100 can be used in beating heart septal defect repair procedures. In some instances, the shaft 110 of the delivery device 100 can be configured to extend and contract with the beating of the heart.

Advancement of the repair device 100 may be performed in conjunction with echo imaging, direct visualization (e.g., direct transblood visualization), and/or any other suitable remote visualization technique/modality. With respect to cardiac procedures, for example, the repair device 100 may be advanced in conjunction with transesophageal (TEE) guidance and/or intracardiac echocardiography (ICE) guidance to facilitate and to direct the movement and proper positioning of the device for contacting the appropriate target cardiac region and/or target cardiac tissue (e.g., an interatrial septum, or any other suitable cardiac tissue). Typical procedures that can be implemented using echo guidance are set forth in Suematsu, Y., *J. Thorac. Cardiovasc. Surg.* 2005; 130:1348-56 ("Suematsu"), the entire disclosure of which is incorporated herein by reference for all purposes.

Figure 4:
FIG. 4 is a flow diagram illustrating a process for closing a septal defect in accordance with one or more examples.
Figure 4:
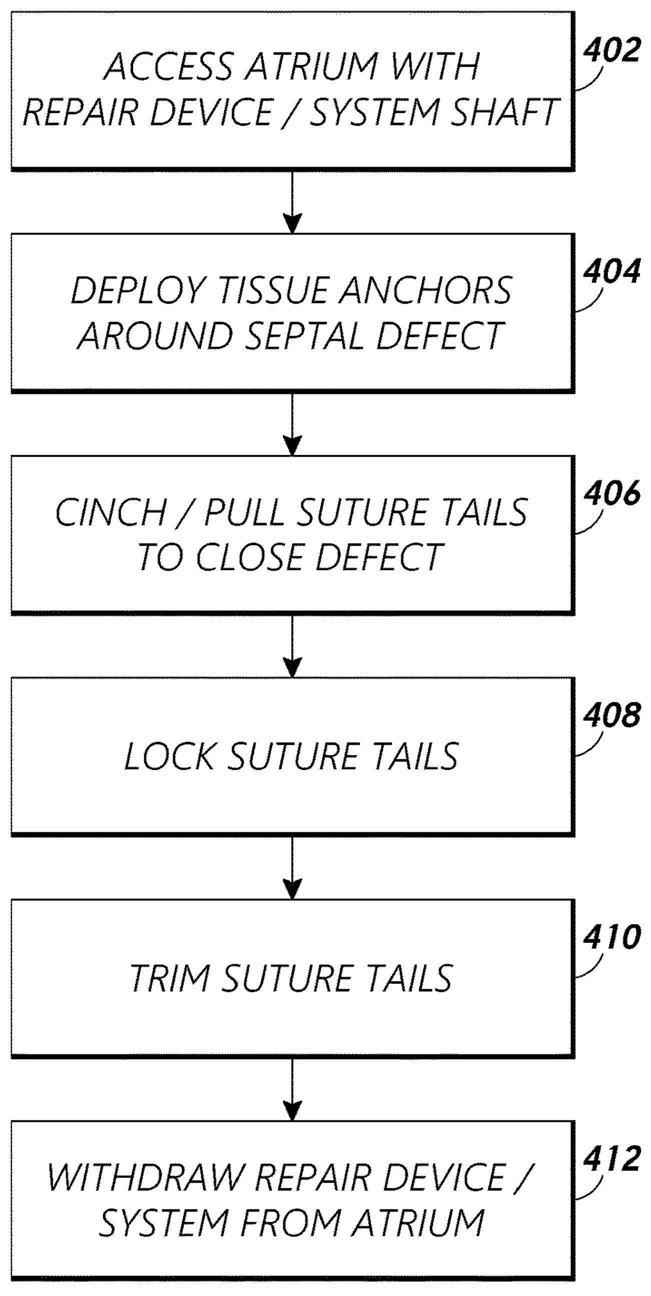

FIG. 4 is a flow diagram illustrating a process 400 for closing a septal defect in accordance with one or more examples. The process 400 may be implemented using transatrial access to the interatrial septum of the patient's heart.

At block 402, the process 400 involves accessing the left or right atrium of the patient's heart with a shaft of a delivery system/device. Such access may be made minimally-invasively through the chest of the patient, such as between adjacent ribs of the patient. In some implementations, an introducer device providing a hemostasis seal may be first punctured through the patient's chest and into the atrium (e.g., left atrium), wherein the shaft of the delivery system may be advanced through a lumen of the introducer to access the target atrium and septum.

At block 404, the process 400 involves deploying two or more tissue anchors in an area around a defect/opening in the atrial septum. Such anchors may be deployed at any position around the defect/opening to provide anchoring positions for drawing the edges of the opening/defect together to thereby at least partially close the opening. The tissue anchors may be deployed on a distal side (e.g., on a right atrial side when access is made to the atrial septum from the left atrium) of the septal wall, or within the septal wall, as described in greater detail below.

At block 406, the process 400 involves cinching/drawing/pulling suture tails associated with the deployed tissue anchors (e.g., deployed in connection with operations associated with block 404) to thereby draw the edges of the opening/defect together to reduce the area of the opening and/or close-off the opening. For example, such cinching may involve pulling suture tails from a plurality of tissue anchors, proximally, together, and/or towards a center (e.g., axial center) of the defect/opening. The suture tails may extend from a side of the septum (e.g., left atrial site) that is opposite the side (e.g., right atrial site) on which the tissue anchors are deployed. Where the tissue anchors are deployed within the septum, rather than on one side or the other thereof, the coupling of the suture tails may be implemented on a side of the septum from which the delivery device/system accessed/contacted the septum. For example, where access to the septum is made via the left atrium, the coupling/cinching of the suture tails together may be implemented on the left atrial side of the septum.

At block 408, the process 400 involves locking or otherwise securing the suture tails in the cinched/tightened configuration, such as through the use of a suture-locking knot, or other locking means/mechanism, such as a clip, clamp, tie, lock, fastener, or the like. Such locking mechanism may be implemented relatively close to the septal wall and/or defect to effectively tighten the suture tails and close the septal defect/opening, and to prevent unnecessary protrusion into the atrial space. Suture-locking knots as described herein may be similar to those described in U.S. Pat. No. 11,065,120, the disclosure of which is hereby explicitly incorporated by reference in its entirety for all purposes.

At block 410, the process 400 involves removing excess suture tails. For example, the portion of the suture tails disposed proximally relative to the locking knot/mechanism (e.g., suture-locking knot) may be superfluous and disposable once locking of the suture tails has been achieved. At block 412, the process 400 involves withdrawing the delivery device/system (e.g., the shaft thereof) from the atrium (e.g., left atrium). The implanted tissue anchors, suture tails, and locking knot/mechanism may be maintained in the septum to thereby hold the defect/opening in a closed-off configuration.

Figure 5:
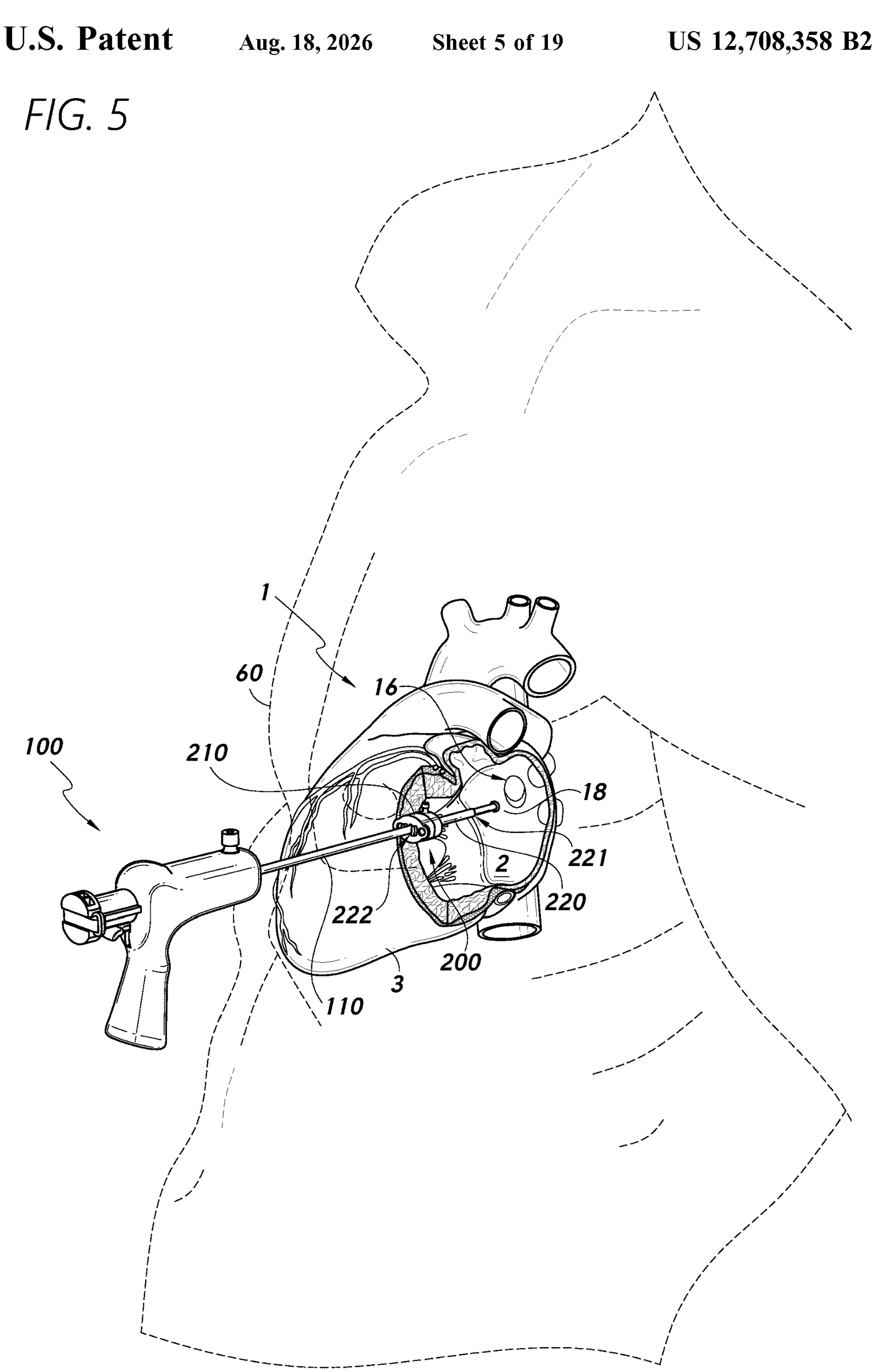
FIG. 5 shows a defect repair device/system accessing an atrial septum through minimally-invasive, transatrial access in accordance with one or more examples.

FIG. 5 shows a defect repair device/system 100 accessing an atrial septum 18 through minimally-invasive, transatrial access in accordance with one or more examples. As referenced above, access to the interatrial septum 18 for the purpose of repairing a septal defect/opening in accordance with aspects of the present disclosure may advantageously be performed minimally-invasively through insertion of a delivery system/device 100 including an elongate shaft 110, which may be inserted into one of the atria (e.g., left atrium 2) through an access path through the chest of the patient, as shown in FIG. 5. For example, the shaft 110 may be insertable through a lumen of an introducer device 200, which may be positioned in the chest 60 and/or heart 1 of the patient to provide access into the atrium in a manner as to preserve hemostasis. In some examples, the access/entry through the chest 60 may be on the anterior portion of the chest, as shown in FIG. 5, which may provide a suitable or desirable access path to the atrium 2. The entry point, although illustrated in FIG. 5 as being on the left side of the patient's chest, may be on either the left or right side and/or provide access to either the left or right atrium. In some implementations, the utilized access may be at any suitable orientation with the target atrium. In some implementations, the access to the target atrium may be in an area of the chest at or near the mid-axillary space, such as in the second or third intercostal space, which may provide suitable access to a septal defect 16 in the atrial septum 18. Access as illustrated in FIG. 5 may be utilized to deploy two or more tissue anchors around the septal defect 16, wherein the septal defect 16 may be substantially closed and/or reduced in size by pulling the deployed tissue anchors together to thereby shorten the distance between the anchors as well as the distance between edges of the defect 16 in the area of the anchors.

The access of the introducer lumen 220 and/or shaft 110 into the atrium 2 may be through an outer wall of the atrium, which may include certain myocardial, epicardial, and/or endocardial layers/tissue. The access may further be through the chest wall, such as between adjacent ribs.

The through-chest access may be achieved by initially making one or more incisions proximate to the thoracic cavity to provide a surgical field of access. The total number and length of the incisions to be made depend on the number and types of the instruments to be used as well as the procedure(s) to be performed. The incision(s) may advantageously be made in such a manner as to be minimally invasive. As referred to herein, the term "minimally invasive" means in a manner by which an interior organ or tissue may be accessed with relatively little damage being done to the anatomical structure through which entry is sought. For example, a minimally invasive procedure may involve accessing a body cavity by a small incision of, for example, approximately 5 cm or less made in the skin of the body. The incision may be vertical, horizontal, or slightly curved. If the incision is located along one or more ribs, it may advantageously follow the outline of the rib(s). Initial access to the heart may be gained by direct puncture (e.g., via an appropriately sized needle, for instance an 18-gauge needle). Access may also be achieved using percutaneous methods, further reducing the invasiveness of the procedure. See, e.g., "Full-Spectrum Cardiac Surgery Through a Minimal Incision Mini-Sternotomy (Lower Half) Technique," Doty et al., *Annals of Thoracic Surgery* 1998; 65 (2): 573-77 and "Transxiphoid Approach Without Median Sternotomy for the Repair of Atrial Septal Defects," Barbero-Marcial et al., *Annals of Thoracic Surgery* 1998; 65 (3): 771-74, the entire disclosures of each of which are incorporated herein by reference for all purposes.

Once needle (e.g., trocar-type needle) access to the atrium 2 has been achieved, a guidewire may be advanced through a lumen of the needle shaft to thereby access the ventricle 2 through the needle. The needle may be proximally withdrawn to thereby remove the needle from the heart wall and from around the guide wire. The guidewire is thereby left in place in the heart wall and partially within the atrium 2. An introducer 200 may be placed over the guidewire and advanced into the atrium 2. The introducer 200 may be inserted with a dilator. The surgeon/practitioner can use one or more sutures to make a series of stiches in one or more concentric circles in the myocardium at the desired location to create a "purse-string" closure. The Seldinger technique, or other process, can be used to access the target atrium in the area surrounded by the purse-string suture. Once the introducer 200 is properly placed, the purse-string suture can be tightened to reduce bleeding around the lumen of the introducer.

The introducer/port device 200 may contain one or more fluid-retention valves to prevent blood loss and/or air entry into the atrium 2. The hemostatic introducer 200 may be inserted into the target atrium at a tip 221 associated with a lumen/shaft 220 of the introducer 200. The lumen 220 of the introducer 200 may be used to guide the shaft 110 of the tissue anchor delivery device/system 100. The body or hub 210 of the introducer 200 may be used to secure the introducer 200 to the pericardium/epicardium of the heart for stable entry of the shaft 110 of the tissue anchor delivery device 100 and/or to control the amount of bleed-back during the procedure. In some instances, a female Luer may be used to de-air the introducer 200 through a port prior to use and/or to connect a fluid flush, such as a heparin flush, during the procedure.

The introducer lumen 220 provides a conduit into the target surgical area/chamber 2. In some instances, the introducer 200 comprises one or more hemostasis valves associated with a channel/lumen port 222. Such hemostasis valve(s) may comprise silicone or other flexible material configured to keep blood from flowing out of the channel/lumen port 222. The port 222 may serve as a tissue anchor delivery device lumen insertion port, wherein an inserted delivery device shaft 110 may pass through the lumen 220 of the introducer 200 and out the distal end 221 thereof for access to the target chamber. The port 222 may further be dimensioned to accommodate insertion of a dilator device used to guide the introducer into the target chamber. The distal end 221 of the introducer 200 may have a tapered shape to seal against the delivery system shaft 110 and to reduce trauma from insertion thereof.

In some implementations, an endoscope may first be advanced through the introducer 200 to visualize the atrium 2 and/or the septal defect 16. By use of an appropriate endoscope, a careful analysis of the septum 18 and septal defect 16 may be performed. For example, each segment/area of the septum around the defect 16 may be carefully assessed to determine its integrity and position relative to the defect 16. Based on this assessment, the practitioner can determine whether the defect 16 can indeed be repaired using a suture-/tissue-anchor-based, minimally-invasive repair procedure, as described in detail herein.

The shaft 110 may present a relatively low-profile repair/delivery device, which may be dimensioned to fit within the lumen 220 of the introducer 200. For example, the shaft 110 may be a 3 mm (9 Fr) shaft. Furthermore, the tip (e.g., end effector) 114 may advantageously be flexible to allow for insertion into the lumen 220 even where the lumen 220 has a smaller diameter than the extended diameter of the tip 114. The advancement of the device shaft 110 may be performed in conjunction with echo imaging and/or direct visualization (e.g., direct transblood visualization). For example, the delivery device 100 may be advanced in conjunction with transesophageal echocardiogram (TEE) guidance or intracardiac echo (ICE) to facilitate and direct the movement and proper positioning of the device.

Figure 6:
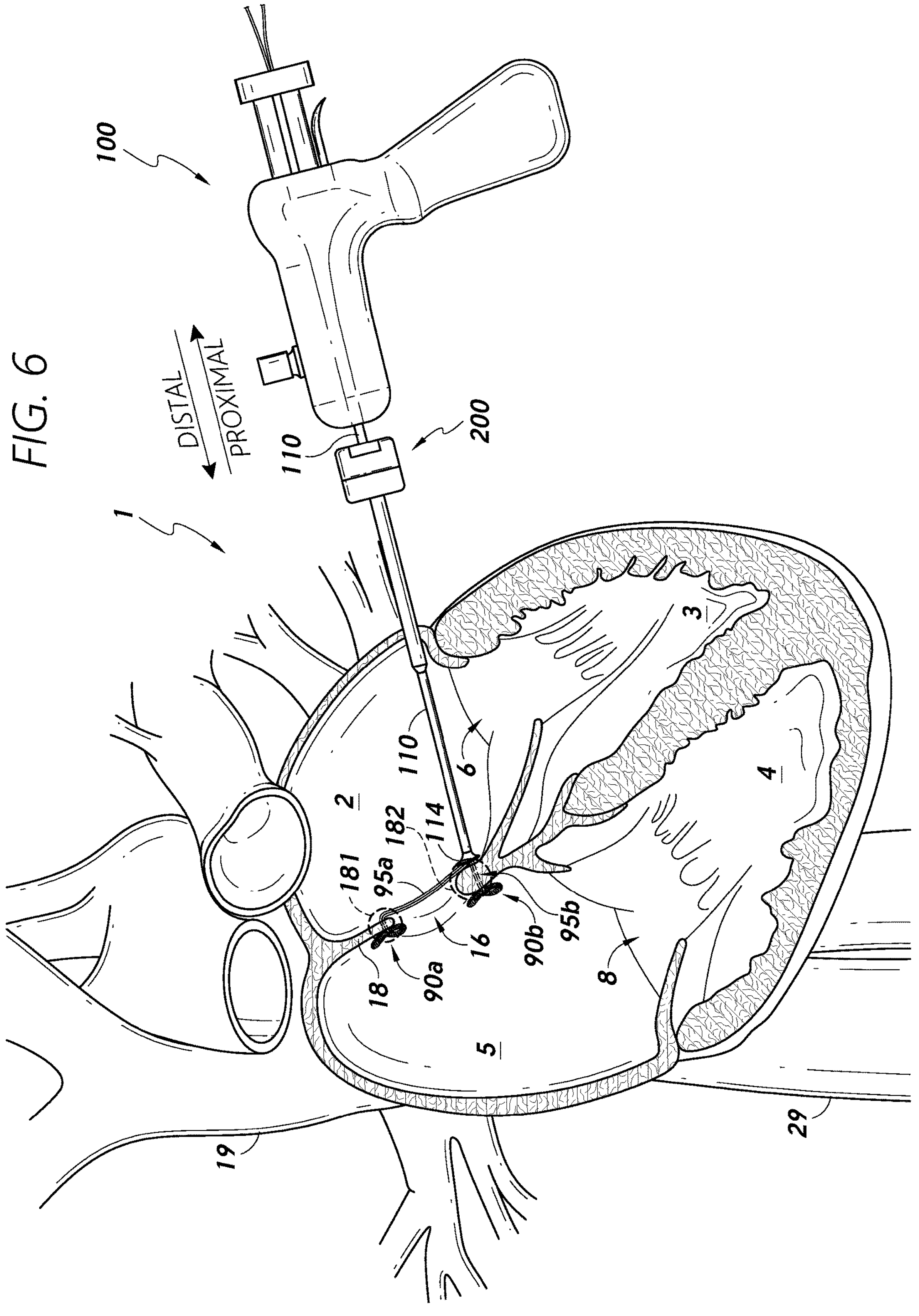
FIG. 6 shows a defect repair device/system deploying suture-connected tissue anchors around a septal defect in accordance with one or more examples.

FIG. 6 shows a defect repair device 100 deploying suture-connected tissue anchors 90 around a septal defect 16 in accordance with one or more examples. The tissue anchor deployment/delivery device 100 may be utilized to deploy two or more anchors 90 in the area of an atrial septum 18 around a septal defect/opening 16. To facilitate such tissue anchor deployment, an introducer 200 may be inserted with a distal portion thereof in the target atrium (e.g., left atrium 2), wherein the introducer 200 provides an access lumen through which an elongate shaft 110 of the delivery device 100 may be inserted into the atrium 2 and approximated to the target atrial septum or other tissue wall 18.

A needle me may be projected from a distal end of the shaft 110 and into and/or through the septal wall 18 to thereby allow for deployment from within and/or on the needle of a tissue anchor on a distal side of the tissue wall with respect to the approach side/angle of the shaft 110, or within the tissue wall 18. Each of the tissue anchors 90 may have associated therewith and/or have emanating therefrom one or more suture tails 95. For example, in some examples, the tissue anchors 90 are formed of knot-type suture forms, as shown in FIG. 6, wherein the suture forms may be formed of one or more sutures that include the suture tails 95. Once the tissue anchors 90 are deployed, the suture tails 95 may be cinched in a manner as to pull the tissue anchors 90 together and/or in a manner as to cause edges of the defect/opening 16 to come together to some degree, to thereby reduce the area of the defect/opening 16.

Although FIG. 6 shows access to the septum 18 via the left atrium 2, wherein the tissue anchors 90 are deployed on the right atrial side of the septum 18, it should be understood that examples of the present disclosure may be implemented using access from the right side of the heart through the right atrium 5, wherein such implementations may involve the deployment of tissue anchors on the left atrial side of the septum 18. Access to the septum 18 from the right atrium may be desirable in some patients or settings due to pressure conditions of the right atrium 5 relative to the left atrium 2. For example, generally, the fluid pressure levels in the right atrium 5 may be less than those in the left atrium 2 in some patients and/or during portion(s) of the cardiac cycle. Therefore, intervention in the right atrium may suffer from less turbulent conditions relative to the left atrium, and therefore may involve a simplified procedure.

The suture tails 95 may be tied together or otherwise clipped or secured together in a tensioned configuration to produce the closing/occlusion effect with respect to the septal defect 16. Any number of tissue anchors 90 may be utilized to close the defect 16. For example, it may be desirable to deploy at least two tissue anchors to allow for edges associated with opposite sides or areas of the defect 16 to be brought together to at least partially close the defect 16. In implementations in which just two tissue anchors are utilized, one or more side orifices may be produced or remain after the tissue anchors are pulled together. However, even where one or more peripheral orifices remain after defect closure, the area of such orifice(s) generally may be substantially reduced relative to the area of the defect 16, such that shunting between the atria is reduced in a beneficial manner. Where two tissue anchors are implemented, it may be desirable to position such tissue anchors at or near a center/midline of the defect to maximize the degree of closure of the defect/perforation 16. In some examples, three or more tissue anchors are implemented to provide closure of the defect from multiple positions around the perimeter thereof, which may increase the degree of closure and/or reduce the amount of shunting.

The suture tails 95 emanate proximally from the respective tissue anchors 90. The first tissue anchor **90*a* may be considered to be deployed/implanted in a first area 181 of the tissue wall 18, which may be in an area near/around the defect 16. The second tissue anchor 90*b* may be considered to be deployed/implanted in a second area 182 of the tissue wall 18, which may likewise be in an area near/around the defect 16. The defect 16 may be formed in the tissue wall 18 at least partially between the anchors 90*a*, 90*b* and/or areas 181, 182, such that pulling the anchors together serves to at least partially reduce the size and/or close the defect 18**.

FIGS. 7-1 and 7-2 show tissue anchors 90 deployed past and within a tissue wall 18, respectively, in accordance with one or more examples. Image 701 of FIG. 7-1 shows a tissue anchor delivery shaft 110 advanced to a septal wall 18 or other tissue wall from a first area or chamber 2 (e.g., left (or right) atrium), wherein a needle 30 or other instrumentation may be utilized to puncture the septum 18 through-and-through such as to allow for deployment on an opposite side (e.g., right (or left) atrial side) of the tissue wall 18 from the puncture side of the wall. Suture tail(s) 95 can be drawn/disposed through the tissue wall 18 and exposed on/in the access side/chamber 2, such that tightening/cinching of the suture tail(s) 95 can be implemented on the access side 2 to effect defect closure. Image 702 shows tenting of the defect wall 18 to provide a secure position for the end effector 114 against the tissue wall 18 for tissue anchor deployment on the opposite side of the wall 18. The image 703 shows the deployed tissue anchor 90 with suture tails 95 associated therewith passing through the tissue wall 18 to the access chamber 2.

The tail(s) 95 emanate proximally The tissue anchor 90, as with any tissue anchor disclosed herein, may be formed of winds of suture in a coil configuration, wherein ends of the coil can be brought together to form one or more loops of coiled suture (two loops shown in a figure-eight configuration for illustration purposes, though it should be understood that the anchors disclosed herein may include a single loop in some examples). The anchor/knot portion 90 and the suture tails 95 may be formed from and/or part of a single line of suture that is wound to form the coils of the tissue anchor/knot portion 90. That is, the knot/anchor portion 90 may be integrated with the suture tail(s) 95.

The device 100 may be used to contact the target septum 18 with the end effector 114 thereof. For example, the target site of the septum 18 may be slowly approached from the left atrial side thereof by advancing the distal end of the shaft 110 without contacting the atrium wall. Once the tip 114 is positioned in the desired position, the distal end of the shaft 110 and the tip 114 may be used to drape, or "tent," the septum 18 to better secure the tip 114 in the desired position, as shown in image 701 of FIG. 7-1. Draping/tenting may advantageously facilitate contact of the tip 114 with the septum 18 throughout one or more cardiac cycles, to thereby provide more secure or proper deployment of tissue anchor(s). The target location/position on the tissue wall 18 may advantageously be located relatively close to the edge of the defect 16 to minimize the likelihood of undesirable reconstruction/deformation of the septum 18.

As shown in image 701, a needle 130 having a tissue anchor associated therewith may be punctured through the septum/wall 18. For example, with the shaft 110 positioned against the wall 18, a plunger/actuator of the tissue anchor delivery device can be actuated to move the needle 130 and/or a pusher disposed within the shaft 110, such that the coiled suture-form portion 191 of the suture anchor 90 slides off the needle 130. A distal piercing portion of the needle 130 punctures the wall 18 and forms an opening therein. In some instances, the needle 130 is projected a distance of between about 0.2-0.3 inches (e.g., between about 5-8 mm), or less, distally beyond the distal end of the shaft 110 (e.g., beyond the tip 114). In some instances, the needle 130 is projected a distance of between about 0.15-0.4 inches (e.g., between about 3-10 mm). In some instances, the needle 130 is projected a distance of about 1.0 inch (e.g., about 2.5 cm), or greater. In some instances, the needle 30 extends until the distal tip of the needle and the entire coiled suture-form 191 extend through the tissue wall 18. While the needle 130 and suture-form 191 are projected into the distal (e.g., right atrium) side of the wall 18, the shaft 110 and tip 114 may advantageously remain entirely on the access side 2 (e.g., left atrium) of the wall 18.

As the pusher (not shown) within the tissue anchor delivery device shaft 110 is moved distally, a distal end of the pusher can move or push the distal coiled suture-form 191 (e.g., pre-deployment coiled portion of the suture anchor 90) over the distal end of the needle 30 and further within the distal area/side of the wall 18 (e.g., right atrium 5), such that the suture-form extends distally beyond a distal end of the needle 30. For example, in some instances, at least half a length of the suture-form 191 extends beyond the distal end of the needle 30. In some instances, at least three quarters of the length of the suture-form 191 extends beyond the distal end of the needle 30. In some instances, the entire coiled suture-form 191 extends beyond the distal end of the needle 30.

Image 702 shows the suture-form tissue anchor 90 deployed on the distal (e.g., right atrial) side of the wall/septum 18. For example, after the suture-form 191 has been pushed off the needle 30, pulling one or more of the suture tail(s) 195 (e.g., suture strands extending from the coiled portion of the suture) associated with the tissue anchor 90 proximally can cause the suture-form 191 to form a bulky knot anchor 90, as shown. For example, the bulky knot suture anchor 90 may be formed by approximating opposite ends of the coils of the suture-form 191 towards each other to form one or more loops. In some instances, two suture tails 195 may extend from the proximal/access side 2 of the wall 18, wherein such tails can be tensioned, locked, and/or otherwise manipulated in the access chamber/area 2.

As referenced above, in some implementations, a tissue anchor deployed for the purpose of closure of a septal defect or other tissue wall opening/perforation may be deployed at least partially within the target tissue wall, as opposed to substantially entirely on one side of the tissue wall as in FIG. 7-1. Image 704 of FIG. 7-2 shows a short-throw needle puncture into the target tissue wall 18 for tissue anchor deployment within the tissue wall. Image 705 shows a tissue anchor 90 deployed at least partially within the tissue wall 18 (e.g., atrial septum or other cardiac tissue wall). Image 706 shows the deployed tissue anchor 90 with suture tails 95 associated therewith passing through the tissue wall 18 into the access chamber 2 from which the tissue anchor deployment shaft 110 approaches the tissue wall. Although shown as including only a single anchor 90 and set of suture tails 95 for clarity, it should be understood that the suture tails 95 and the implementations associated with FIGS. 7-1 and 7-2 can be joined and/or cinched together with suture tail(s) of another tissue anchor deployed in an area around the defect 16. In both the case of FIGS. 7-1 and 7-2, the anchor/knot 90 and/or suture tail(s) 95 may be considered to be deployed in the tissue wall 18, whether the anchor/knot is disposed at least partially within the wall 18 or entirely on the distal side of the wall 18 when deployed.

Figure 8:
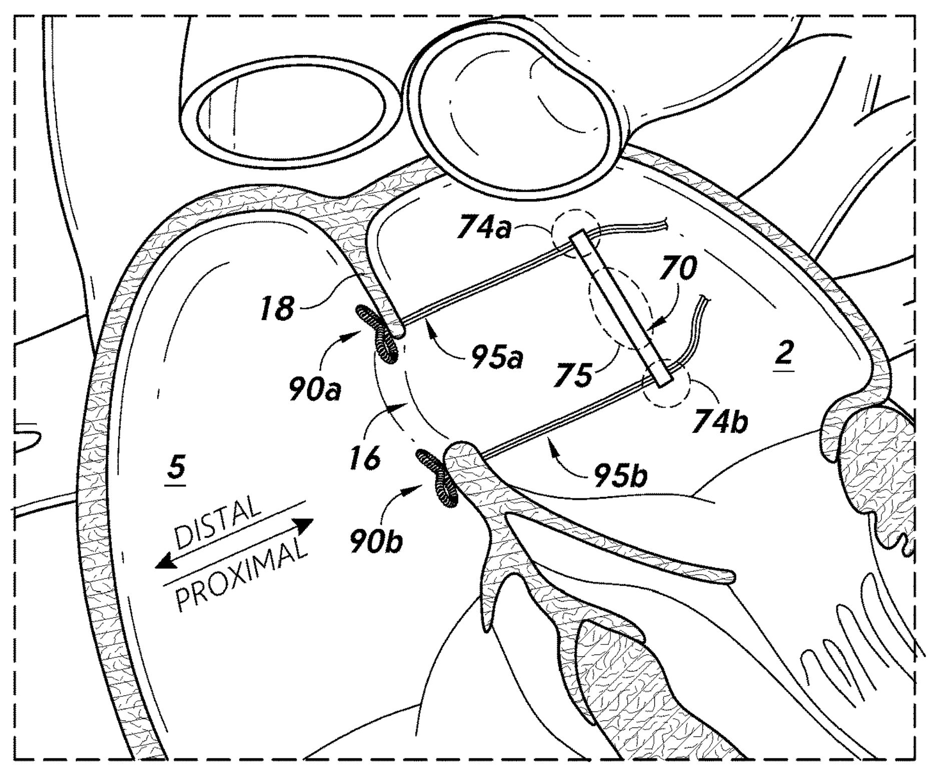
FIG. 8 shows a plurality of suture tails disposed through a defect occluder patch in accordance with one or more examples.

The present disclosure includes detailed description of various procedures for closing septal defects and other openings in tissue walls by tightening suture tails associated with deployed tissue anchors in a manner as to draw the edges of the opening/defect towards one another to reduce the size of the opening. Additionally or alternatively, certain devices, such as patches, wireframes, and/or other occluder forms/structures may be utilized to cover over at least a portion of a defect/opening, wherein such occlusion device is held in place against the opening by coupling with suture tails of one or more tissue anchors deployed in accordance with aspects of the present disclosure (e.g. using a shaft-type tissue anchor delivery/deployment device). FIG. 8 shows a plurality of suture tails 95 disposed through a defect occluder patch 70 in accordance with one or more examples. Use of a patch/occluder in connection with tissue-anchor- and suture-based defect closure in accordance with aspects of the present disclosure may be particularly suitable for occlusion of relatively large openings/defects. With the sutures 95 passed through the peripheral areas of the patch/occluder 70, such positioning may advantageously allow for desirable amount of separation between the areas 74 of suture coupling to the patch 70.

FIG. 8 shows a plurality of tissue anchors **90*a*, 90*b* (collectively 90) deployed, wherein each of the tissue anchors has respective suture tail(s) or other line(s) 95*a*, 95*b* associated therewith and projecting/exposed on an opposite side of the tissue wall 18 as the anchors 90. In some implementations, a patch or other occluder device/structure (e.g., wire mesh or frame, cloth, or other rigid or flexible structure) may be coupled to the suture tails 95 in some manner to thereby secure, at least in part, the patch 70 to the suture tail(s) 95. For example, in some examples, the suture tails 95 may be threaded through portions of the patch/occluder 70. For example, such threading or passing-through of the suture tails through the patch/occluder 70 may be in a peripheral/outer area of the patch 70 to thereby allow for a central/medial portion thereof to be disposed between the tissue anchors 90 and/or associated suture tails 95**.

In FIG. 8, the patch/occluder 70 is disposed about and/or coupled to the suture tails 95, wherein the patch 70 is positioned away from the defect/opening 16 in the tissue wall 18, such that a portion of the suture tails 95 is disposed between the patch/occluder 70 and the tissue wall 18 and/or defect/opening 16. In some examples, the patch/occluder 70 may be advanced into the atrium or other target chamber/area 2 in a compressed (e.g., rolled) configuration within a shaft of a tissue anchor delivery device, which may be similar to any of the shafts/delivery devices disclosed herein. Such delivery system components are not shown in FIG. 8 for visual clarity, though it should be understood that the patch/occluder 70 may be introduced to the target anatomy using such a device. A pusher (e.g., elongate shaft/rod) may be implemented within a delivery system/device shaft to push the patch 70 distally along the suture tails 95 to advance the patch 70 to the defect 16.

Figure 9:
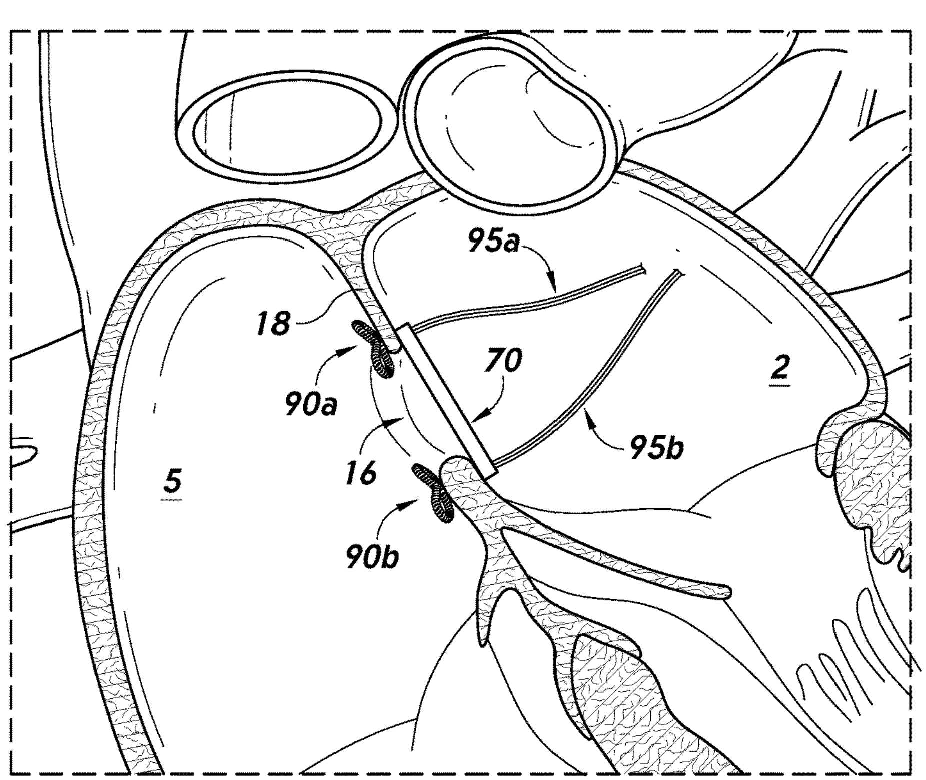
FIG. 9 shows an occluder patch covering a septal defect in accordance with one or more examples.

FIG. 9 shows an occluder patch 70 covering a septal defect 16 in accordance with one or more examples. In accordance with the septal defect closure procedure reflected in FIG. 9, the patch/occluder 70 may be further advanced along the length of the suture tails 95 until it reaches/abuts the target tissue wall 18 and/or defect 16. Such advancement of the occluder/patch 70 may be implemented in accordance with any suitable or desirable procedure or mechanism. For example, a pusher device may be implemented within a delivery system shaft, wherein advancement of the pusher device in a distal direction may effect, at least in part, distal advancement of the patch 70.

Once the patch 70 is advanced to at least partially cover the opening 16 in the tissue wall 18, relevant procedures may involve locking or securing the patch/occluder 70 to the suture tails 95 in such position to thereby maintain the patch/occluder 70 over the opening 16 to occlude, at least in part, the opening 16. In some implementations, the patch 70 is secured in place using deployable suture-locking suture-form knot(s), or other mechanical fastener (e.g., plastic or metal court block/fastener).

Figures 1, 10:
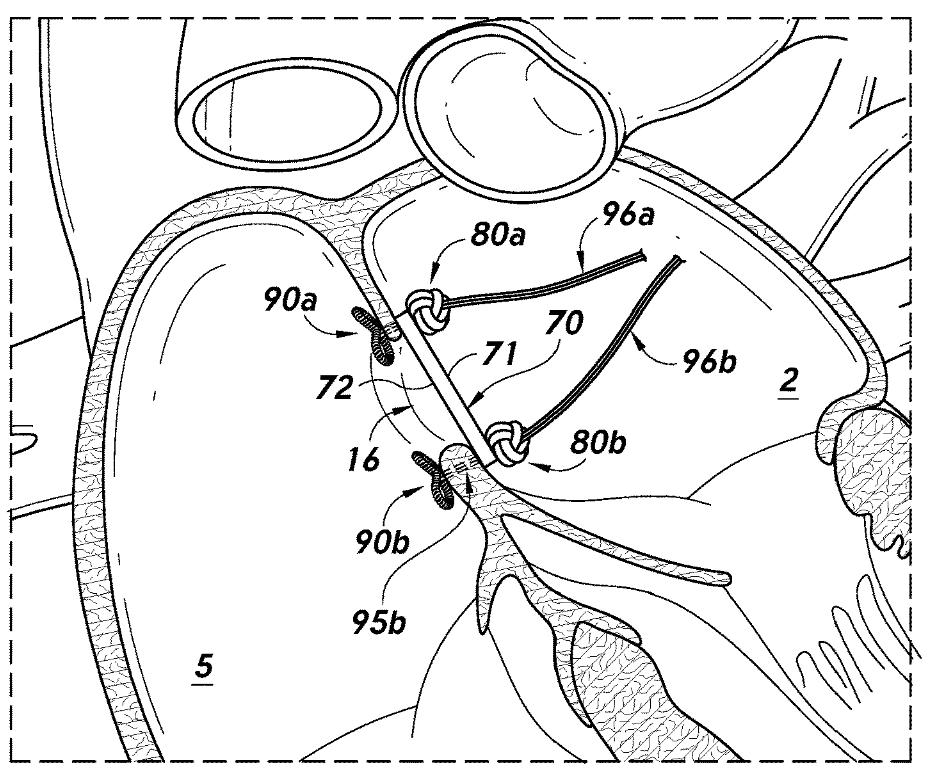
Figures 2, 10:
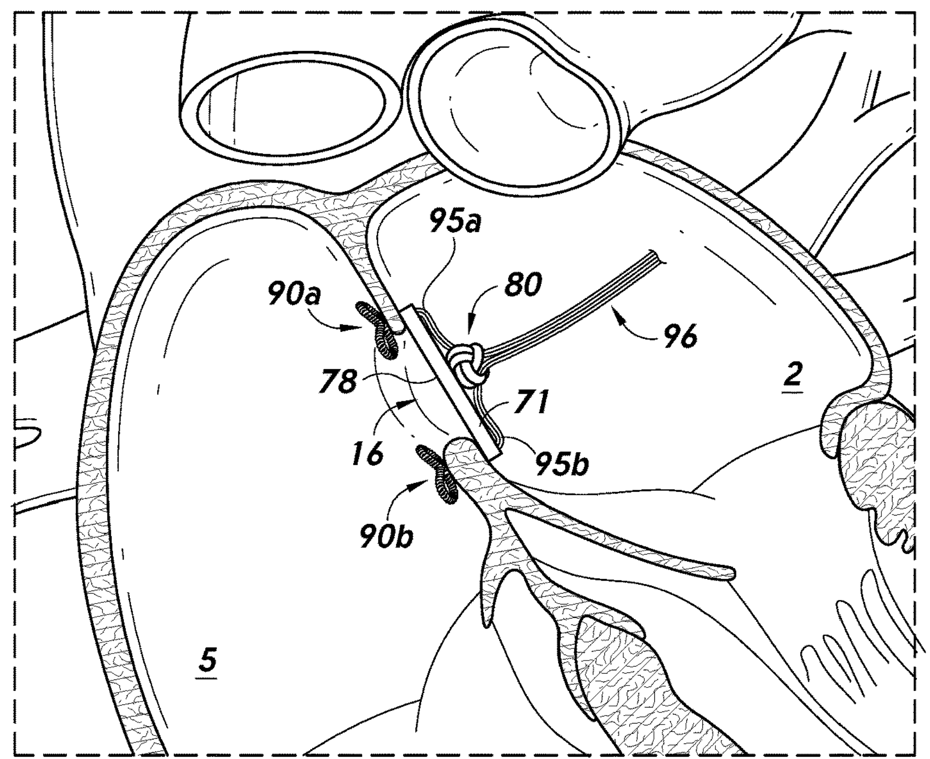

FIGS. 10-1 and 10-2 show an occluder patch 70 secured over a septal defect 16 in accordance with one or more examples. Such locking or securing of the patch/occluder 70 to the suture tails 95 may be implemented in any suitable or desirable way. For example, FIG. 10-1 shows an implementation in which one or more locks 80 lock the suture tails 95 against the proximal side 71 of the patch 70, wherein each group of suture tails 95 (e.g., each set of one or more suture tails associated with a separate respective tissue anchor 90) is locked with a separate locking means/mechanism 80. The locks 80 may be any suitable or desirable type of lock, such as a suture-form lock, clip, clamp, cord-lock, fastener, or the like. In the image of FIG. 10-1, suture-form locks 80 (also referred to herein as suture-locking knots) are implemented, wherein such locking knots may be slid over the suture tails 95 and tightened in position against the proximal side 71 of the patch/occluder 70, as shown. With the locks in place, the excess suture tail portions 96 may extend proximally from the locks 80 until, and up to the length where, such suture portions are trimmed/removed.

FIG. 10-2 shows an alternative locking implementation, in which a single lock 80 is used to lock the suture tail(s) 95 emanating from multiple tissue anchors 90 together. For example, the lock 80 may be secured/tightened on suture tails 95 against a backside 71 of the patch/occluder 70. The lock 80, for example, may be positioned in a central position with respect to the backside 71 of the patch 70 between the tissue anchors 90*a*, 90*b*, or may be positioned at any other position on the back/proximal side 71 of the patch 70. In the implementation shown in FIG. 10-2, the proximal suture tail portions 96 emanating proximally from the lock 80 may be effectively joined together prior to trimming/removal thereof. As in other examples of the present disclosure, the suture fasteners 80 of FIGS. 10-1 and 10-2 can essentially be locked in place by assuming the locked configuration in which the suture tail(s) are held therein.

Figures 1, 11:
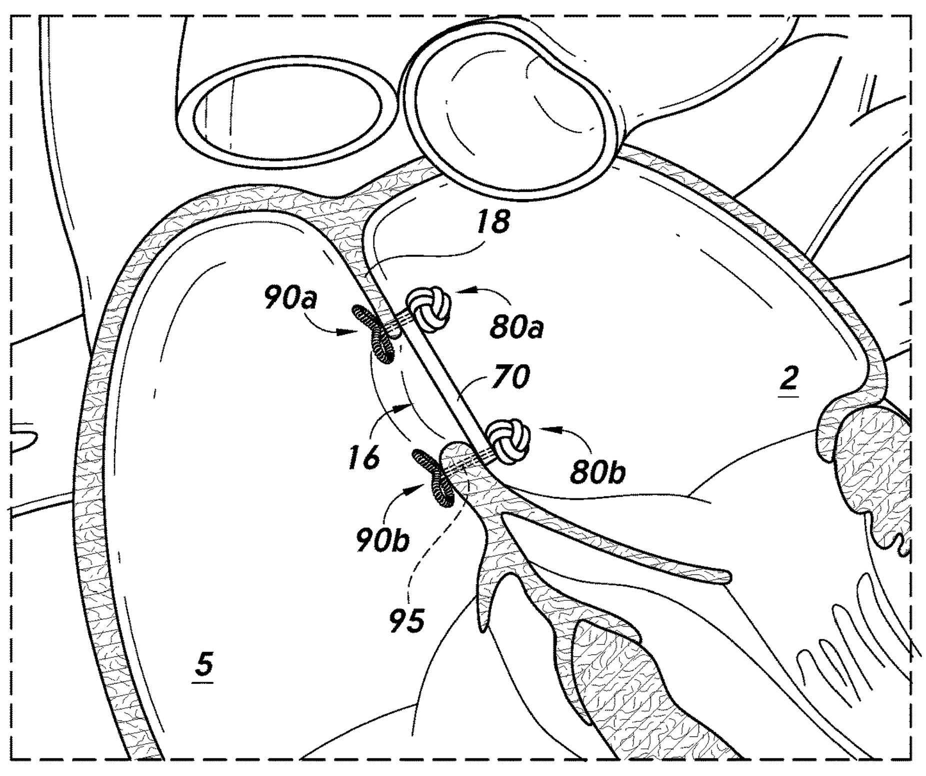
Figures 2, 11:
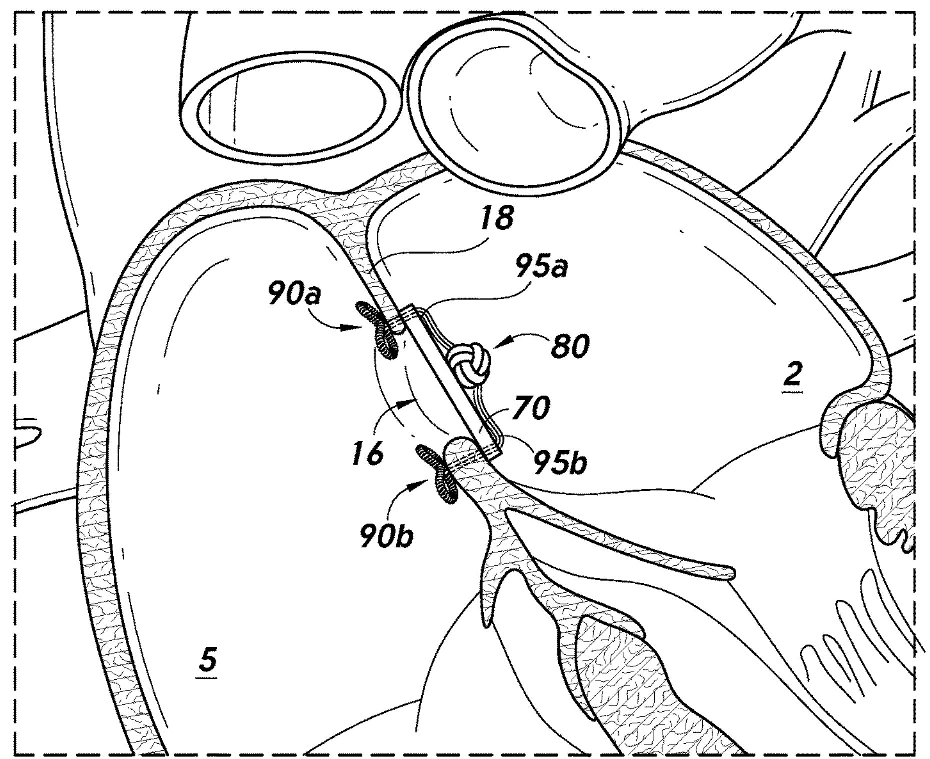

FIGS. 11-1 and 11-2 show a suture-secured occluder patch 70 implanted over a septal defect 16 in accordance with one or more examples. In the images of FIGS. 11-1 and 11-2, the proximal suture tails/portions 96 have been removed/cut-off, thereby leaving the tissue anchor 90, suture 95, patch 70, and lock 80 assembly implanted in the target tissue wall 18 as a permanent or semi-permanent implant.

Figure 12:
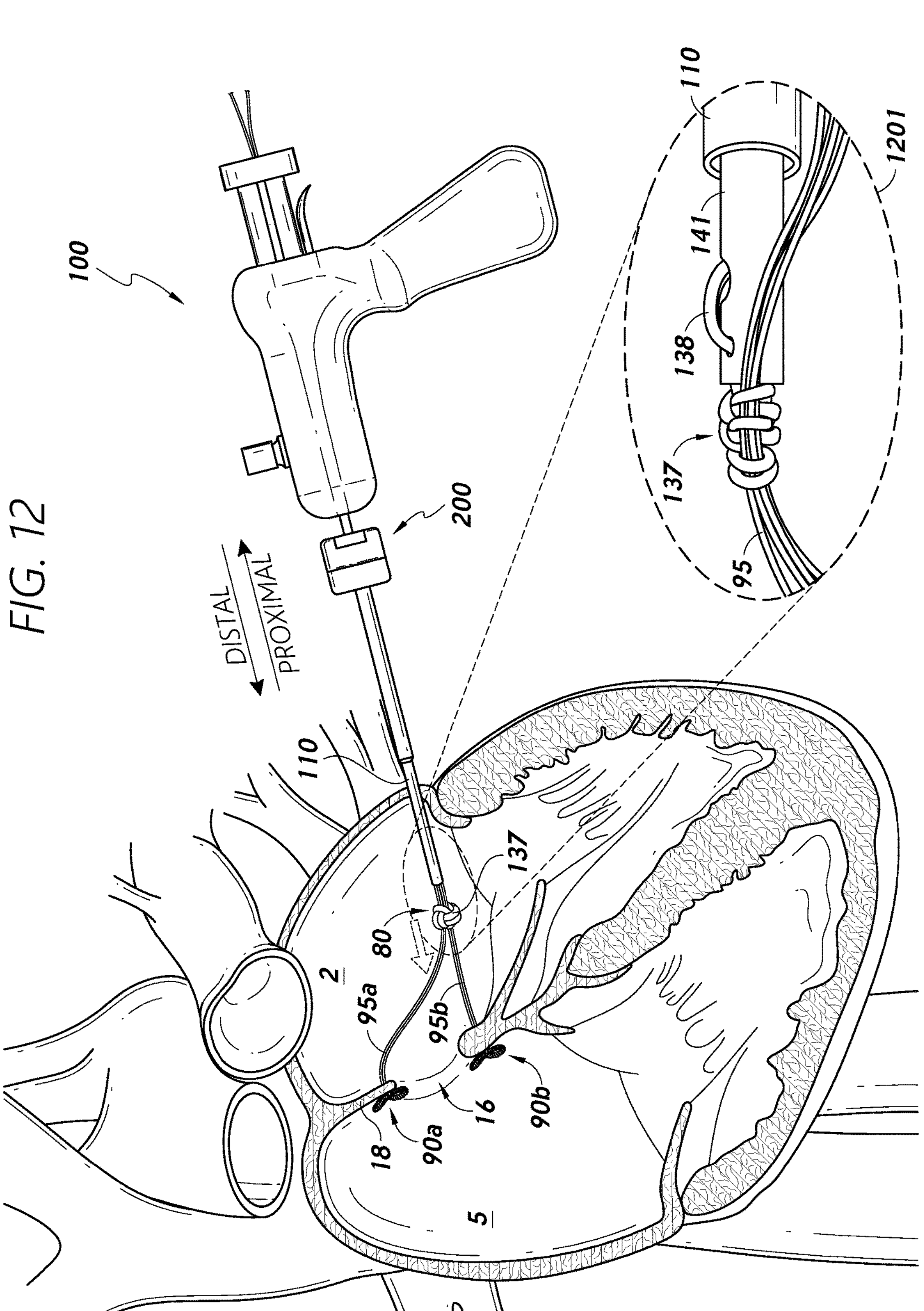
FIG. 12 shows a suture-locking knot being advanced over suture tails anchored around a septal defect in accordance with one or more examples.

As described above, locking means implemented to lock suture tails associated with tissue anchors in a cinched configuration to thereby at least partially close a septal defect or other opening in a tissue wall may comprise one or more suture-form, knot-type fasteners/locks. For example, FIG. 12 shows a delivery system 100 comprising an elongate shaft 110 that is advanced to the target anatomy (e.g., left atrium 2) through a hemostatic introducer 200, wherein the delivery device/system 100 may be utilized to deploy a suture-locking knot 137 (wherein the suture-locking knot 137 is a particular type of lock 80 that may be implemented in accordance with examples of the present disclosure) over suture tails 95 associated with respective tissue anchors 90 implanted/deployed in a target tissue wall 18, wherein the locking knot 137 may be used to close/cinch the suture tails 95 and/or knots 90 together to thereby at least partially close a tissue defect 16 (e.g., atrial septal defect). FIG. 12 shows the suture-locking knot 137 being advanced over the suture tails 95 that are anchored around the septal defect 16. Advancing the suture-locking knot 80 (or other suture fastener) can serve to bring the deployed tissue anchors 90*a*, 90*b* closer together, thereby reducing the size of the defect opening 16.

In some examples, the proximal portion/ends of the tethered cord/suture tails 95 are threaded through the deployable locking knot 137 and pass to the outside of the heart, and/or outside of the patient's body. The suture tails 95 may be inserted/passed into/through the windings of the knot 137, wherein the knot 137 is configured to hold tension and/or close/cinch around the suture tails 95 in a manner as to provide sufficient frictional engagement with the suture tails to secure the knot 137 at a specific coupling position with respect to the suture tails. In some implementations, the knot 137 can be tightened around the suture tails 95 to the degree to reduce or eliminate the risk of slipping/sliding along the suture tails after implantation thereof.

With the suture tails 95 passed through the suture-form locking knot 137, the suture tails/strands 95 may be used as a guide to slide the knot 137 to advance the knot towards the tissue anchors 90, wherein as the knot 137 approaches the tissue anchors 90, the tissue anchors may be brought together to thereby at least partially close the opening 16. The steps associated with FIGS. 12 and 13 may be implemented/performed while visualizing the target anatomy under echocardiography or other imaging modality.

The suture-locking knot 137 can advantageously provide a mechanism to knot, join, secure, and/or approximate multiple sutures together in various medical applications in addition to septal defect repairs. The locking suture/knot 80 can include a knot portion 137 configurable between a delivery configuration and a deployed configuration, and a tether portion extending proximally from the knot portion 137 and configured to be manipulated outside the target region/area 2 to transition the knot portion 137 within the target region 2 from its delivery configuration to its deployed configuration. The locking suture 137 can be secured to the plurality of suture tails 95. Translating or moving the locking suture 137 distally and/or proximally along the free ends of the sutures 95*a*, 95*b* can change the distance between the implants/anchors 90*a*, 90*b*, and therefore the edges of the defect 16. Once a targeted tissue or implant approximation is achieved, the locking suture 137 can be locked by transitioning the knot portion 137 from its delivery configuration to its deployed configuration using a tether portion proximally coupled to the knot 137.

The locking suture 137 can be formed of any suitable material. In some instances, for example, the locking suture can made of one or more of expanded polytetrafluoroethylene ("ePTFE") suture, polybutylate-coated polyester suture, or polyester suture (such as, for example, Ethibond Excel® Polyester Suture, Johnson & Johnson, New Brunswick, New Jersey). In some instances, the locking suture can be modified to increase its coefficient of friction to improve its locking capability. The locking suture, made from ePTFE for example, can be braided, twisted, or knotted (e.g., with overhand knots). Additionally, or alternatively, in some instances, the locking suture's thickness and/or surface texture (e.g., textured surface, coating, etc.) can be configured to increase its coefficient of friction and/or improve its locking capabilities.

The knot portion 137 of the locking suture when in its delivery configuration (as shown in the detailed image 1201) can be slidably coupled to and delivered (e.g., pushed distally) along the suture portions 95 using a delivery device that is operated from outside the target region 2 (e.g., controlled remotely and delivered minimally invasively). The knot portion 137 can be in the form of braided, twisted, coiled, looped, and/or knotted lines (e.g., sutures). In a delivery configuration, the knot portion 137 can be loose enough to allow the suture tails 95 to slide therethrough. In a delivery configuration, the knot portion 137 can be constricted to create a tortuous path for the plurality of sutures passing through the knot portion. For example, the knot portion 137 can be in the form of one or more multi-turn coils distributed about various regions of the suture tails 95, and the coils can be changed from an elongated, delivery configuration, in which the knot portion 137 is slidable, translatable, and/or pushable along or about the suture tails 95 while maintaining its integrity (e.g., its coiled formation), to a deployed configuration by constricting the coils and/or approximating opposite ends of the coil(s) towards each other to lock or secure the knot portion 137 to the suture tails 95 and inhibit relative motion therebetween.

To deploy/lock the knot portion 137, the tether portion associated with the knot 137 can be pulled proximally, which may cause the knot portion 137 to constrict on the suture tails 95 so that they are secured together within the knot portion 137 at a desired position/tension. In addition, the knot portion 137 can be secured in a way that it does not move distally or proximally along the suture tails 95. With the knot portion 137 secured or locked to the suture tails 95 at a targeted location, the suture tails 95 and the tether portion 138 extend to a location outside the target chamber/anatomy 2. In this configuration, the tether portion 137B and the free ends of the suture tails 95 can be coupled to and secured at any position relative to the tissue wall.

The knot portion 137 may be positioned at the distal end of a knot holder 1041 prior to deployment. The detailed image 1201 shows the knot portion 137 of the locking suture at the distal end of a knot holder component 141, which may be deployed/advanced within the shaft 110, with the suture tails 95 threaded through the knot.

As shown in the image 1201, the suture tails 95 can be passed through the locking suture 137, which may be coupled to an end of the repair device shaft 110. In some examples, the suture tails 95 can be threaded through portions of the locking suture 137. In some examples, the suture tails 95 can pass through a central portion of the locking suture 137 (e.g., a lumen formed by one or more coils of the locking suture 137). The shaft 110 (or other component of the system/device 100) can be used to push, urge, slide, translate or otherwise move the knot portion 137 in its delivery configuration distally along the suture tails 95. As the shaft 110 further urges the knot 137 distally towards the wall 18 and/or defect 16, the point of intersection of the suture tails 95*a*, 95*b* can be moved towards the anchors 90, tissue wall 18, and defect 16, such that the lengths of the suture tail portions 95 between the knot 137 and the anchors 90 shorten.

When the knot (or other lock means) 137 is positioned in a desirable position, such that the tissue anchors 90 are desirably brought together to close the defect 16, a tether portion 138 associated with the knot 137 can be pulled proximally to deploy the knot portion 137. Deployment/locking of the knot 137 inhibits relative movement between the knot 137 and the suture tail portions 95 disposed therein. Advantageously, locking the knot 137 does not significantly increase or alter the tension on the suture tails 95 and, consequently, the force or tension on the tissue anchors 90 and the tissue wall 18 does not significantly change during deployment of the knot portion 137.

Figure 13:
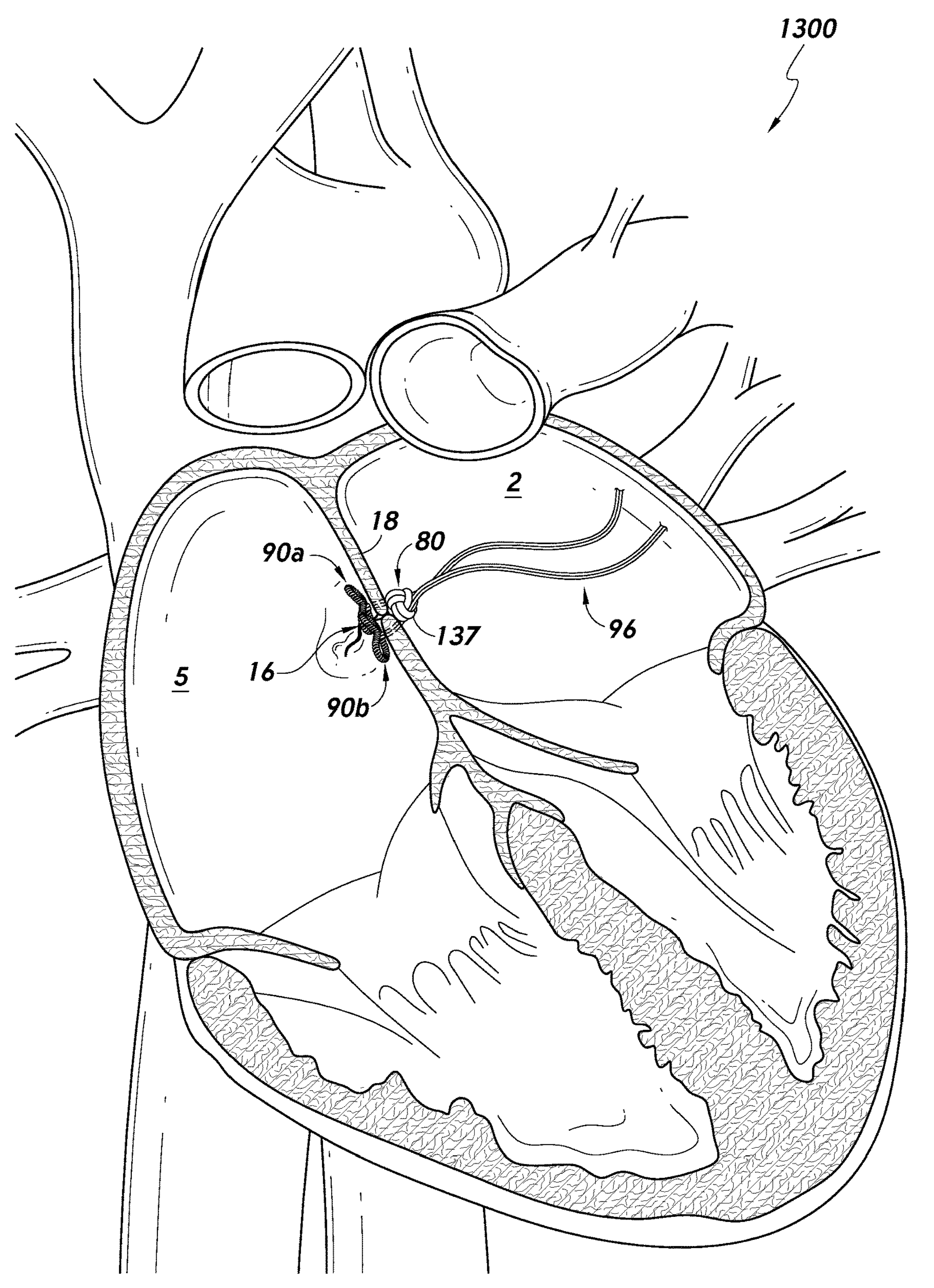
FIG. 13 shows a suture-locking knot in a tightened configuration in accordance with one or more examples.

FIG. 13 shows a suture-locking means 80, shown and described as a suture-locking knot 137, in a tightened configuration with the locking knot 137 cinched against the access side (e.g., left atrial side) of the tissue wall 18 (e.g., septal wall). The tissue anchors 90*a*, 90*b* and associated suture tails 95*a*, 95*b* that pass through the tissue wall 18 are drawn together to close the opening/defect 16 or at least partially reduce an area thereof. After the knot 137 (or other suture-locking means as described herein) is locked in place, the proximal suture tail portions 96 can be removed or trimmed-down to some extent to reduce the amount of free material/suture exposed in the atrium 2. In some examples, such cutting of the suture tails 96 can be performed using the delivery device 100, which may incorporate a cutting mechanism, such as at a distal end of the shaft 110.

As described in detail above, various examples of the present disclosure involve using a delivery device/system comprising an elongate shaft through which a needle or other puncture tool/instrument can be advanced and deployed from a distal end of the elongate shaft, wherein a suture-form disposed on the needle may be deployed from the needle and tightened to form a suture-form knot-type tissue anchor. With respect to procedures involving the deployment/implantation of a plurality of tissue anchors around a defect/opening in a tissue wall for the purpose of defect closure as described herein, some examples of the present disclosure provide for multi-anchor deployment using a plurality of suture-form-tissue-anchor-equipped needles disposed within a single shaft of the delivery device/system.

Figure 14:
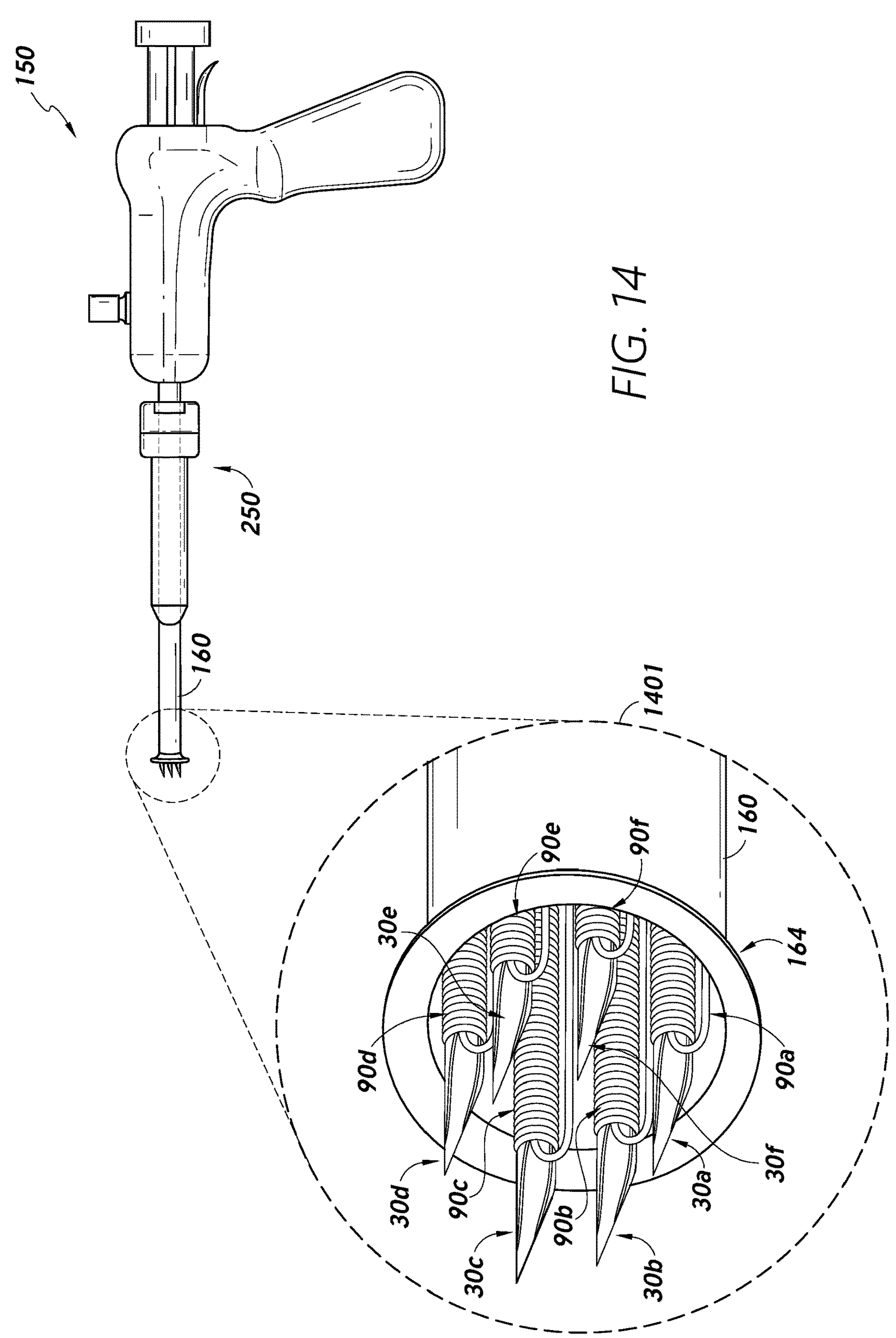
FIG. 14 shows a defect repair device including a multi-needle tissue anchor deployment shaft in accordance with one or more examples.

FIG. 14 shows a defect repair device 150 including a multi-needle tissue anchor deployment shaft 160 in accordance with one or more examples. The shaft 160 may be utilized for tissue anchor deployment, wherein the shaft 160 may have a diameter greater than that of other examples disclosed herein in order to accommodate a plurality of needles arranged in a parallel manner within the shaft 160, as shown in the detailed image 1401 of the distal end of the shaft 160 shown in FIG. 14. Each of the needles 30 may have wound thereabout a respective suture-form 90, which may be configurable to form a bulky-knot-type tissue anchor as described in detail herein. For example, proximally pulling a suture tail or portion associated with a respective suture-form 90 may cause the suture-form to form a shape (e.g., figure-eight-type shape) presenting a relatively wide area suitable/effective for anchoring retention on a side of the tissue wall, as described herein. Defect repair using the multi-needle delivery device/system 150 may be particularly suitable for open-heart surgical procedures due to the relatively larger diameter of the shaft 160, or access to the target anatomy may be made through an introducer 250 dimensioned to accommodate the larger-diameter shaft 160. Although FIG. 14 shows the shaft 160 disposed in an introducer device 250, for open-heart surgical operations, such introducer may not be implemented or necessary.

As referenced above, the elongate shaft 160 of the delivery device 150, due to the relatively greater diameter thereof compared to other delivery devices disclosed herein, may be implemented with an introducer device 250 that likewise has a relatively greater diameter to accommodate passage through a lumen thereof of the elongate shaft 160 having a plurality of parallel needles 30 disposed therein. In some examples, the shaft 160 includes a plurality of at least partially separated or partitioned lumens or channels, wherein each of the needles 30 is disposed within and/or passed through a separate one of the lumens/channels. Each of such lumens/channels may be configured to receive a needle 30 carrying a suture-form tissue anchor 90.

The implementation of delivery systems for septal defect repair or other tissue defect closure/repair, wherein such delivery systems include shafts housing multiple tissue anchor deployment needles, can reduce the amount of time and/or effort associated with a defect closure procedure and/or increase the ease-of-use for delivering/deploying multiple tissue anchors (e.g., suture knot tissue anchors). With reference to the detailed image 1401 of FIG. 14, where multiple needles 30 are arranged in an at least partially circular arrangement, examples of the present disclosure may provide for sequential needle projection/deployment in a circular fashion. In some examples, a single engagement or advancement of a plunger component of the delivery device/system 150 may cause sequential and/or simultaneous deployment of a plurality of the needles 30.

FIGS. 15-1, 15-2, and 15-3 provide a flow diagram illustrating a process 1500 for repairing a septal defect using a multi-needle repair device in accordance with one or more examples. FIGS. 16-1, 16-2, and 16-3 provide images of cardiac anatomy and certain devices/systems corresponding to operations of the process 1500 of FIGS. 15-1, 15-2, and 15-3 in accordance with one or more examples.

The procedure 1500 and delivery device 150 may be particularly suitable for closure/repair of openings in tissue walls that are relatively small, which may allow for the distal end of the shaft 162 be disposed at least partially over the defect/opening, such that the needles may individually be punctured through the edges/periphery of tissue around the opening without having to reposition the shaft 160 between tissue anchor deployments.

At block 1502, the process 1500 involves advancing a multiple-needle delivery system shaft 160 to a septal defect 16, or other target tissue wall opening/defect. For example, the operation(s) associated with block 1502 may involve introducing the shaft 160 into an atrium, such as the left atrium 2, of a heart and approximating and/or contacting the end effector 164 or other distal end portion of the shaft 160 to the tissue wall 18 at least partially over the defect 16, as shown in image 1602 of FIG. 16-1.

At block 1504, the process 1500 involves deploying multiple needles 30 from the delivery shaft 160 and sliding multiple suture-form anchors 90 off of respective ones of the needles 30, wherein such tissue anchor deployment and needle puncture are in an area around the defect/opening 16 in the tissue wall 18 (e.g., interatrial septum).

Figures 1, 15, 16:
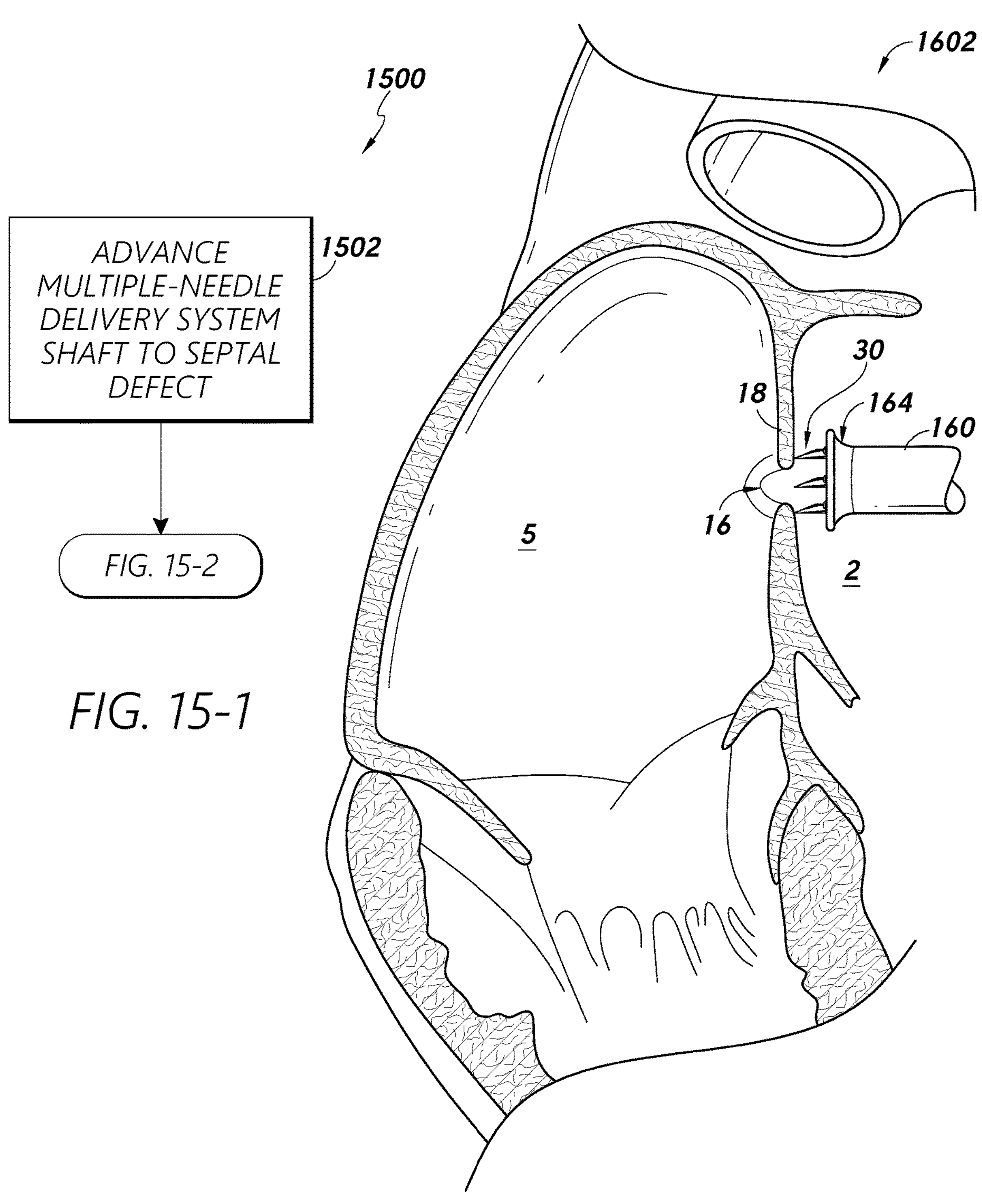
Figures 2, 15, 16:
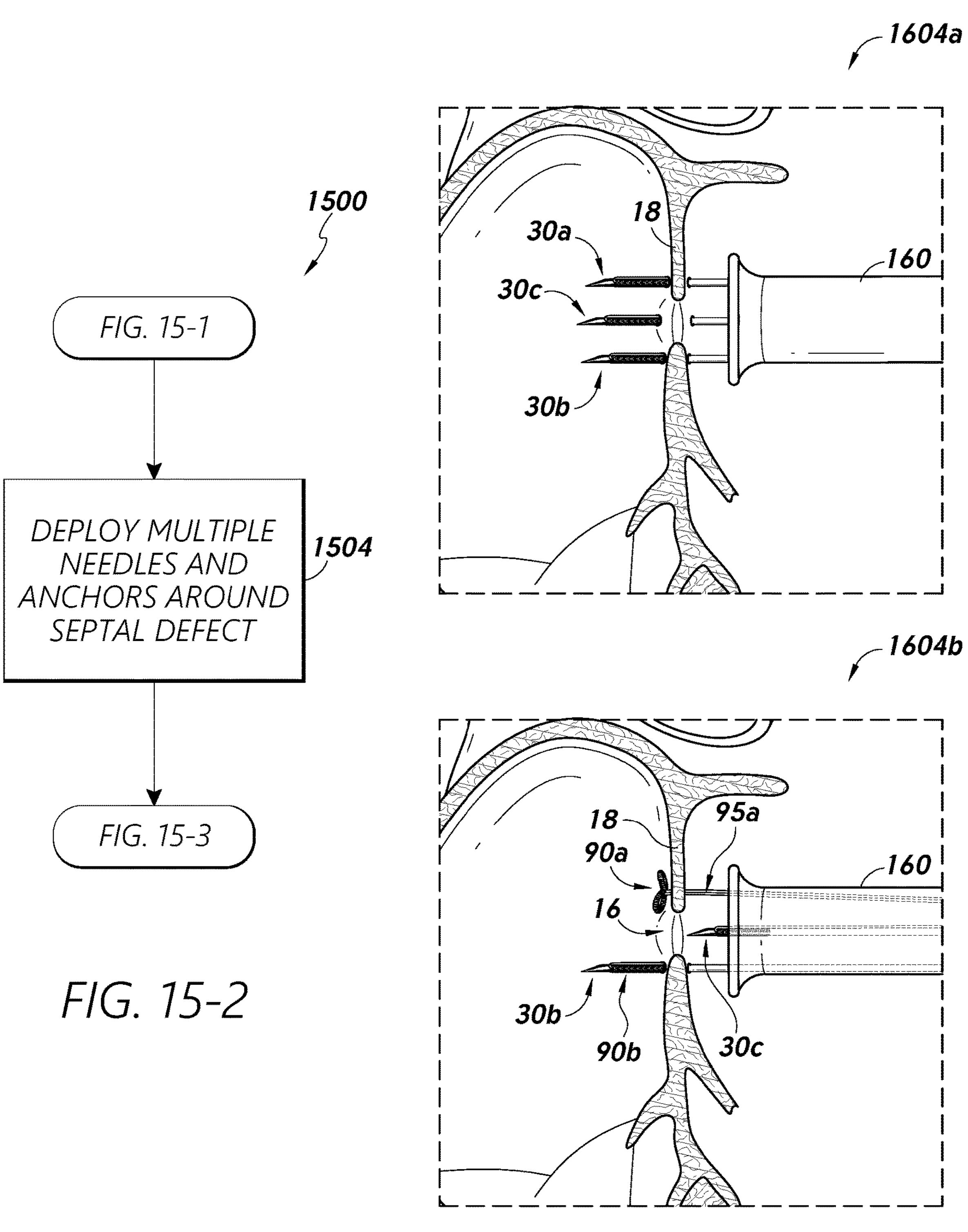
Figures 3, 15, 16:
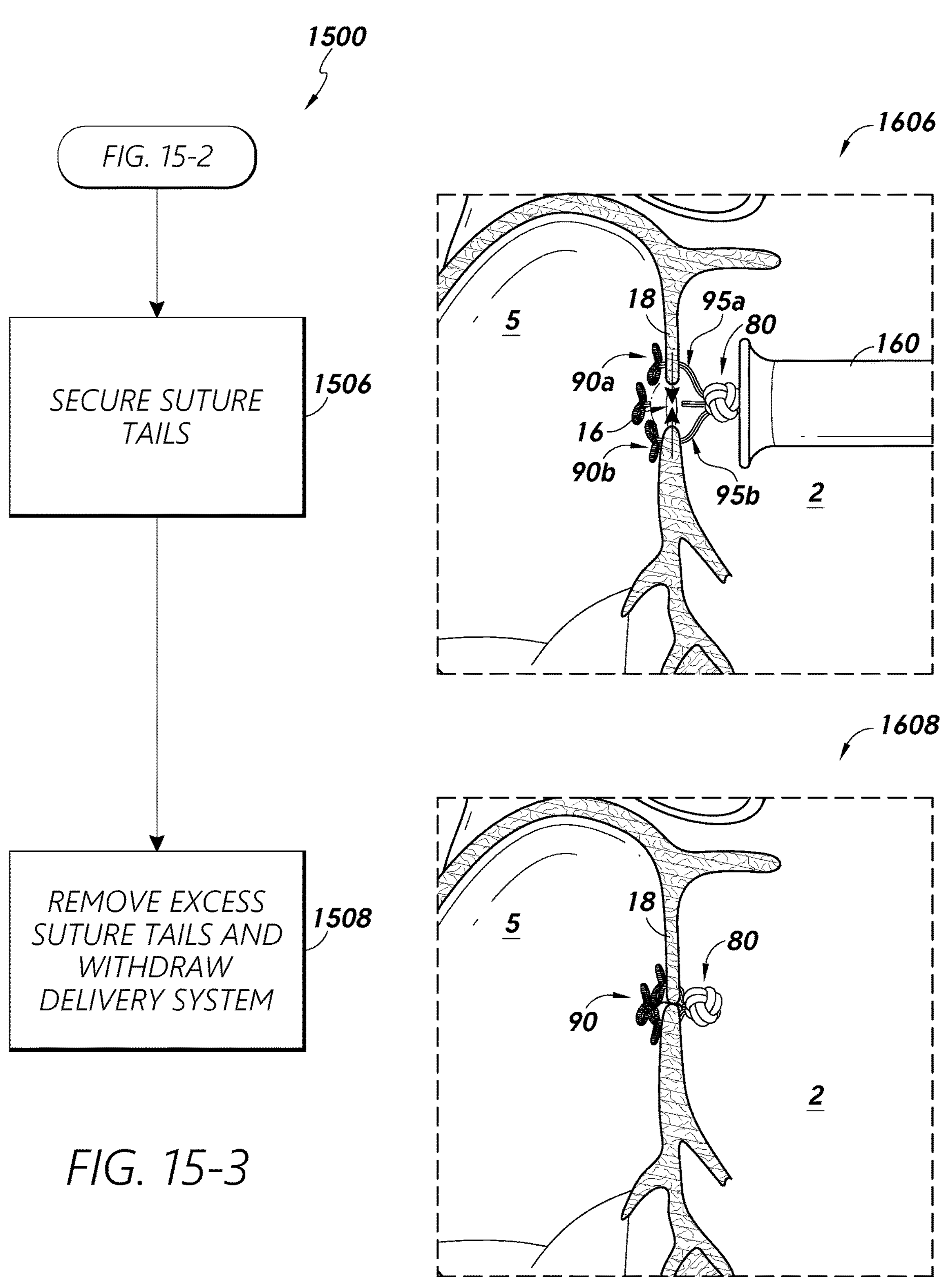

Multiple needle/anchor deployment may be implemented in any suitable or desirable fashion. For example, image 1604*a* of FIG. 16-2 shows simultaneous needle puncture of a plurality of needles through the tissue wall 18, such that tissue anchor deployment and/or needle puncture may be implemented simultaneously with respect to separate needles and tissue anchors of the system. Image 1604*b* shows an alternative implementation in which sequential needle puncture and/or tissue anchor deployment is implemented. For example, a first tissue anchor 90*a* may be deployed prior to deployment of a second tissue anchor 90*b*, and so forth. Furthermore, the needle punctures of the respective needles 30*a*, 30*b*, etc., may be implemented sequentially in order to effect such sequential tissue anchor deployment.

At block 1506, the process 1500 involves securing and/or cinching the suture tails 95 together in a manner as to bring the edges of the defect/opening 16 closer together, to thereby reduce the area of, and/or otherwise close-off, the opening 16. For example, as shown in image 1606 of FIG. 16-3, a suture locking knot or other fastener/fixation means or mechanism 80 may be deployed over the suture tails 95 and advanced distally from the shaft 160 towards the tissue wall 18 in order to draw the tissue anchors 90 together. The locking mechanism 80 may be locked in some manner once the tissue anchors have been cinched/tensioned in a desirable manner.

At block 1508, the process 1500 involves removing excess suture tails that project proximally from the suture lock 80 to thereby reduce the amount of free material within the chamber 2 (e.g., left atrium). The delivery device/system may be withdrawn from the heart or other anatomy/chamber, thereby leaving the tissue anchors 90, suture tails 95, and locking means 80 implanted as an indefinite, permanent, and/or semipermanent implant assembly/device to improve cardiac function, as shown in image 1608 of FIG. 16-3.

Figures 1, 2, 3, 17:
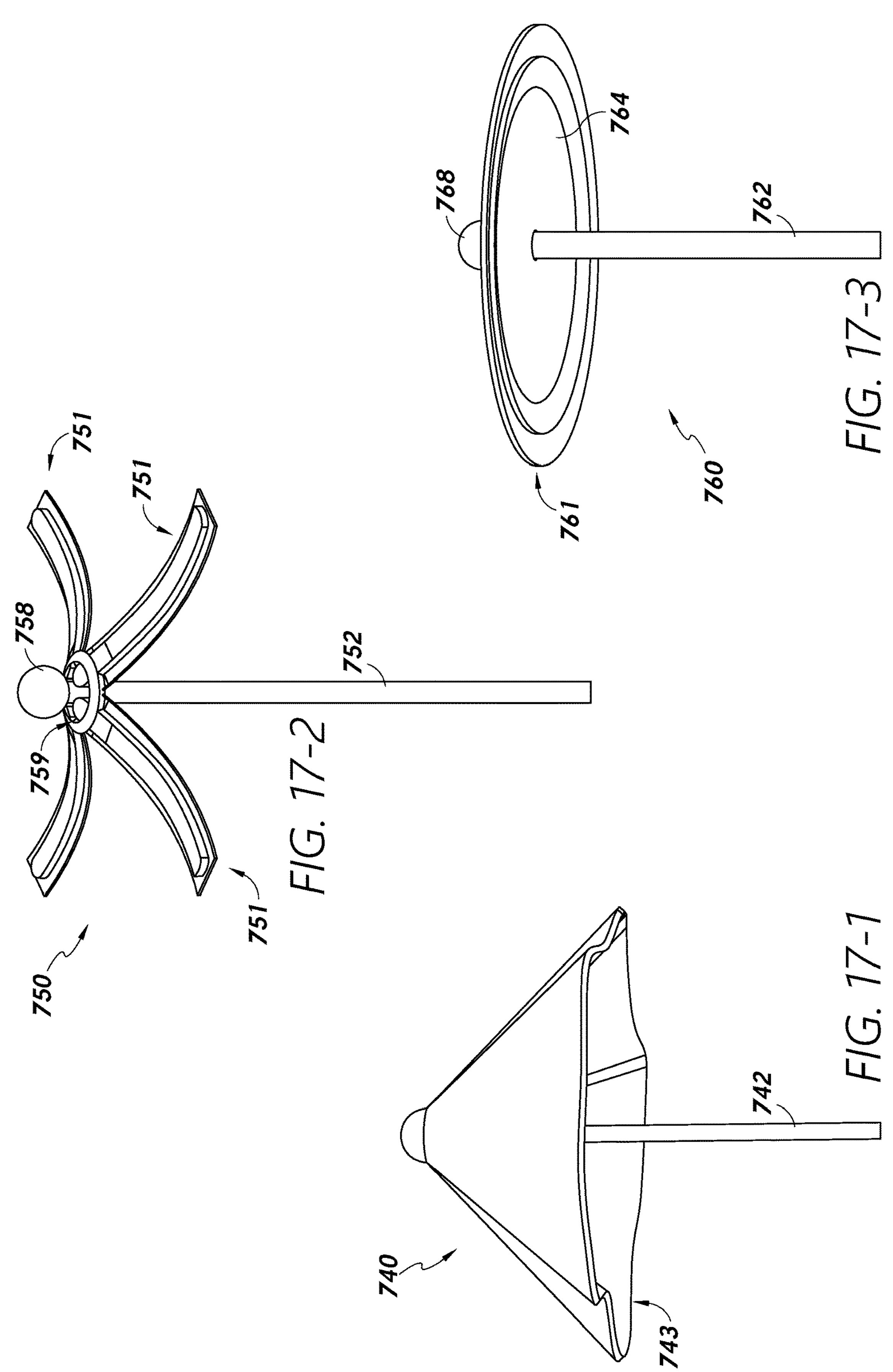
Figures 5, 17:
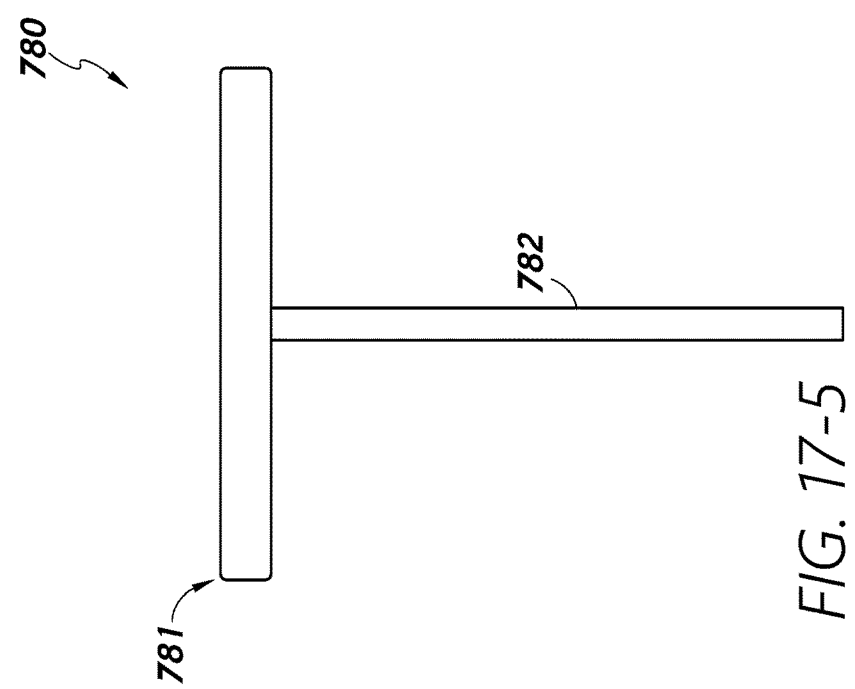
Figures 4, 17:
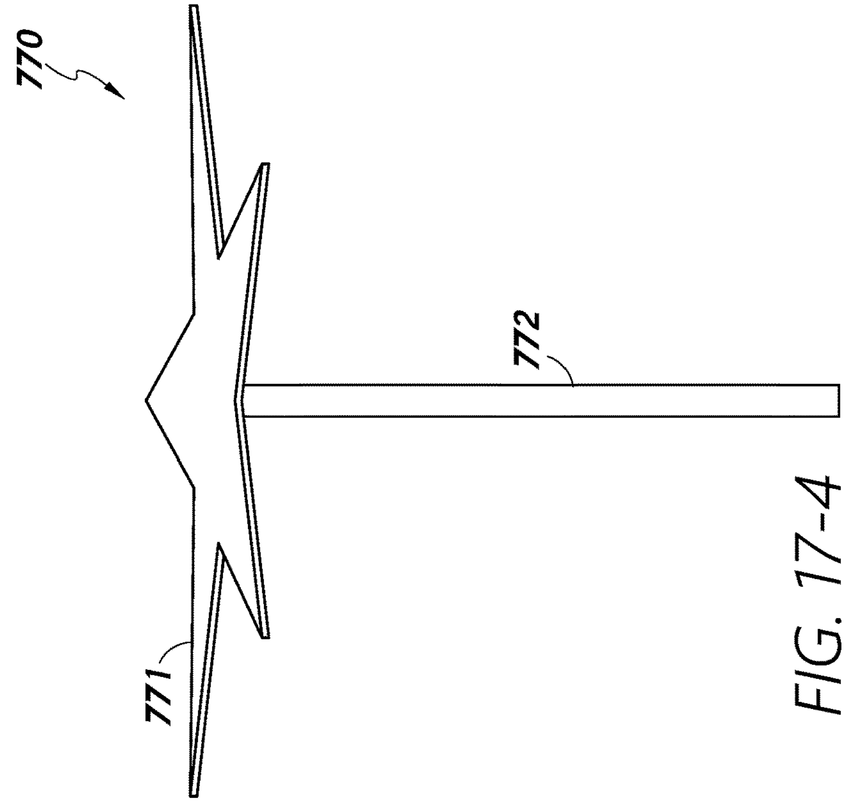

FIGS. 17-1 through 17-5 show tissue anchors that can be used for defect closure in accordance with one or more examples. That is, although bulky-knot-type tissue anchors are illustrated and described in the present disclosure in connection with certain examples, any suitable or desirable tissue anchors may be implemented in connection with examples of the present disclosure; FIGS. 17-1 through 17-5 show examples of tissue anchors that may be implemented.

FIG. 17-1 shows an expandable tissue anchor 740, which may be referred to as an 'umbrella' anchor. FIG. 17-1 shows the expandable tissue anchor 740 in a partially collapsed/deployed configuration. In this example, during delivery of the tissue anchor 740, the interior walls of a lumen of a needle or other shaft can retain the tissue anchor 740 in an elongated delivery configuration when the tissue anchor 740 is disposed within the lumen. The tissue anchor 740 can be coupled to a suture 742 and removably coupled to or otherwise in operable contact with a pusher of the delivery system. The tissue anchor 740 can be delivered in a collapsed/elongated configuration and moved to a radially-expanded deployed configuration by pulling the suture 742 proximally and/or moving a pusher distally. As the tissue anchor 740 is moved distally and the open-end portion 743 exits the delivery device, the tissue anchor 740 is allowed to expand (e.g., the open end 743 opens) towards its deployed or expanded configuration.

In an alternative example, a tissue anchor can be configured similar to the tissue anchor 740 except that the tissue anchor can be disposed on the suture 742 such that the open end of the umbrella shaped portion is distal to the rounded distal end of the tissue anchor. In such an example, the rounded distal end can define a hole through which the suture can be extended and secured. The tissue anchor can be formed with for example a shape-memory material such that the tissue anchor has a biased expanded or deployed configuration and an elongated collapsed configuration when constrained within a delivery device. The tissue anchor can be pushed or moved out of a delivery device with, for example, a pusher device. As the tissue anchor exits a distal end of the delivery device, the tissue anchor can transition from its elongated collapsed configuration to its expanded, deployed or biased configuration. Said another way, as the tissue anchor exits the distal end of the delivery device, the open end of the tissue anchor opens to its expanded or biased configuration. In this manner, the tissue anchor can transition from its delivery configuration to its deployed configuration as it exits the delivery device.

FIG. 17-2 shows an example of an expandable tissue anchor 750, which includes elongate members 751 with free ends and a stopper receiving section 759. In an elongated delivery configuration in which the anchor 750 is disposed within a lumen defined by a delivery device, the free ends of the elongate members 751 can be disposed proximal to the stopper receiving section 759. In a deployed configuration, the elongate members 751 are radially expanded/projecting, as shown in FIG. 17-2. The anchor 750 includes a suture 752 having a distal/terminal stopper 758 disposed through the stopper receiving section 759, which cooperatively mates with the stopper 758. During delivery of the tissue anchor 750, the interior walls of the delivery shaft can retain the tissue anchor 750 in its elongated delivery configuration. The tissue anchor 750 can be coupled to a suture 752 and removably coupled to or otherwise in operable contact with a pusher. The tissue anchor 750 can be delivered in the elongated delivery configuration and moved to the radially-expanded deployed configuration by pulling the suture 752 proximally and/or moving the pusher or other deployment component distally. In this manner, the stopper 758 associated with the suture 752 can be moved into contact with the stopper receiving section 759, and the stopper 758 and the stopper receiving section 759 can collectively facilitate the transition of the tissue anchor 750 from the elongated delivery configuration to the expanded deployed configuration.

In an alternative example, a tissue anchor can be configured similar to the tissue anchor 750 except that the tissue anchor can be disposed on the suture 752 such that the free ends of the elongate members are distal to the stopper receiving section. In such an example, the tissue anchor can be formed with for example a shape-memory material such that the tissue anchor has a biased expanded or deployed configuration and an elongated collapsed configuration when constrained within a delivery device. The tissue anchor can be pushed or moved out of a delivery device with, for example, a pusher device. As the tissue anchor exits the delivery device, a distal end of the tissue anchor can transition from its elongated collapsed configuration to its expanded, deployed or biased configuration. Said another way, as the tissue anchor exits the distal end of the delivery device, the free ends of the elongate members can extend radially towards the deployed or biased configuration of the tissue anchor. In this manner, the tissue anchor can transition from its delivery configuration to its deployed configuration as it exits the delivery device.

The tissue anchor 750 can be formed of any suitable material, such as, for example a malleable stainless steel, a shape memory or superelastic alloy, or a polymer. One such polymer, for example, can include polyaryletherketones (PAEKs) such as polyether ether ketone (PEEK). Optionally, in some examples, a tissue anchor can include or be coupled to a material (e.g., a fabric and/or polymer) that is configured to distribute an anchor load, cover and/or seal the hole made in the leaflet, and/or promote ingrowth or an otherwise desirable biological response when the tissue anchor is disposed within a heart.

FIG. 17-3 shows an example disc-type tissue anchor 760, which may comprise a disc-type form 761 associated with a suture 762, wherein the form 761 serves to hold the anchor 760 against a tissue wall. In this example, a distal end portion of the suture 762 includes a stopper 658. A radial support member 764 can be coupled and disposed proximal to the proximal end portion of the tissue anchor 760. The radial support member 764 can prevent or otherwise limit the tissue anchor 760 from undesirably flipping or deflecting beyond a plane defined by the stopper 758, and/or distal to the stopper 758. The radial support member 764 can be made of any suitable material sufficient to provide radial support, such as, for example, a non-elastic material. In a deployment configuration, the tissue anchor 760 can be pre-configured to have a slight angle, as shown.

FIG. 17-4 shows another example of a tissue anchor 770 comprising a retention form 771 coupled at a distal end of a suture 772. The retention form 771 may lie at least partially in a transverse plane with respect to an axis of the suture 772. The retention form 771 may have any suitable or desirable shape, such as the illustrated star shape, which may provide desirable retention capability due at least in part to the projecting points of the star.

FIG. 17-5 shows yet another example of a tissue anchor 780, which may be considered a 'T-fastener' anchor. The tissue anchor 780 can be coupled to a suture or sutures 782 and removably coupled to or otherwise in operable contact with a pusher during delivery. The tissue anchor 780 can be delivered in an elongate delivery configuration and moved to an expanded deployed configuration, as shown in FIG. 17-5, by pulling the suture 782 proximally to rotate the retention portion 781 such that the retention portion 781 is non-parallel with respect to the pusher and/or suture 782.

Additional Description of Examples

Provided below is a list of examples, each of which may include aspects of any of the other examples disclosed herein. Furthermore, aspects of any example described above may be implemented in any of the numbered examples provided below.

Example 1: A method of repairing a septal defect, the method comprising advancing an elongate shaft into an atrium of a heart of a patient through an outer atrial wall of the heart, contacting an atrial septum of the heart with a distal end of the elongate shaft, deploying a plurality of tissue anchors from the elongate shaft in tissue of the atrial septum, and cinching suture tails associated with the plurality of tissue anchors to at least partially close a defect in the atrial septum.

Example 2: The method of any example disclosed herein, in particular example 1, further comprising locking the suture tails in a cinched configuration.

Example 3: The method of any example disclosed herein, in particular example 2, further comprising advancing a suture fastener distally over the suture tails, wherein said locking the suture tails involves locking the suture fastener.

Example 4: The method of any example disclosed herein, in particular example 1, further comprising cutting-off proximal portions of the suture tails.

Example 5: The method of any example disclosed herein, in particular example 1, wherein the plurality of tissue anchors comprises three or more tissue anchors.

Example 6: The method of any example disclosed herein, in particular example 1, wherein the plurality of tissue anchors comprise suture-form knot anchors.

Example 7: The method of any example disclosed herein, in particular example 6, wherein each of the suture tails is integrated with a respective one of the suture-form knot anchors.

Example 8: The method of any example disclosed herein, in particular example 1, wherein said advancing the elongate shaft into the atrium is via a minimally-invasive access through a chest wall of the patient, between adjacent ribs.

Example 9: The method of any example disclosed herein, in particular example 1, further comprising puncturing the outer atrial wall with a lumen of an introducer, wherein said advancing the elongate shaft into the atrium is through the lumen of the introducer.

Example 10: The method of any example disclosed herein, in particular example 9, wherein the introducer comprises one or more hemostasis valves.

Example 11: The method of any example disclosed herein, in particular example 1, wherein said deploying the plurality of tissue anchors involves puncturing the atrial septum with one or more needles deployed from the elongate shaft, and pushing the plurality of tissue anchors off the one or more needles.

Example 12: The method of any example disclosed herein, in particular example 11, wherein the one or more needles comprises a first needle and a second needle, each of the first and second needles, prior to said pushing, has winds of suture of one of the plurality of tissue anchors disposed about a distal portion thereof, and said puncturing the atrial septum involves simultaneously deploying at the first and second needles from the elongate shaft.

Example 13: A method of repairing a defect in a tissue wall, the method comprising contacting a tissue wall with a distal end of a rigid elongate shaft, deploying a plurality of tissue anchors from the elongate shaft in the tissue wall, and cinching suture tails associated with the plurality of tissue anchors to at least partially close a defect in the tissue wall.

Example 14: The method of any example disclosed herein, in particular example 13, further comprising advancing a locking means over at least a portion of the suture tails, and locking the locking means on the at least a portion of the suture tails to hold the suture tails in a cinched configuration.

Example 15: The method of any example disclosed herein, in particular example 14, wherein said advancing the locking means causes the plurality of tissue anchors to be brought closer together.

Example 16: The method of any example disclosed herein, in particular example 14, wherein the locking means comprises a suture-locking knot.

Example 17: The method of any example disclosed herein, in particular example 16, wherein the suture-locking knot is configured to slide over the suture tails in an unlocked configuration, and be tightened to a locked configuration in which the suture tails are held in a secured relative position to one another.

Example 18: The method of any example disclosed herein, in particular example 13, wherein said deploying the plurality of tissue anchors involves deploying the plurality of tissue anchors on a distal side of the tissue wall.

Example 19: The method of any example disclosed herein, in particular example 13, wherein said deploying the plurality of tissue anchors involves deploying the plurality of tissue anchors at least partially within the tissue wall.

Example 20: The method of any example disclosed herein, in particular example 13, wherein each of the plurality of tissue anchors comprises a knot portion and two suture tail portions that are formed of a common line of suture.

Example 21: A method of repairing a defect in a tissue wall, the method comprising contacting a first area of a tissue wall with a distal end of an elongate shaft, deploying a first tissue anchor from the elongate shaft at least partially through the tissue wall in the first area, the first tissue anchor having one or more first suture tails emanating proximally therefrom, contacting a second area of the tissue wall with the distal end of the elongate shaft, deploying a second tissue anchor from the elongate shaft at least partially through the tissue wall in the second area, the second tissue anchor having one or more second suture tails emanating proximally therefrom, and pulling the one or more first suture tails and the one or more second suture tails together to at least partially close a defect in the tissue wall, the defect being formed in the tissue wall at least partially between the first area and the second area.

Example 22: The method of example 21, wherein said deploying the first tissue anchor involves deploying the first tissue anchor at least partially within the tissue wall in the first area.

Example 23: The method of example 21, wherein said deploying the first tissue anchor involves deploying the first tissue anchor on a distal side of the tissue wall, wherein the one or more first suture tails pass through the tissue wall to a proximal side of the tissue wall.

Example 24: A method of repairing a defect in a tissue wall, the method comprising contacting a first area of a tissue wall with a distal end of an elongate shaft, deploying a first tissue anchor from the elongate shaft at least partially through the tissue wall in the first area, the first tissue anchor having one or more first suture tails, contacting a second area of the tissue wall with the distal end of the elongate shaft, deploying a second tissue anchor from the elongate shaft at least partially through the tissue wall in the second area, the second tissue anchor having one or more second suture tails, and distally advancing a patch over the one or more first suture tails and the one or more second suture tails to at least partially cover a defect in the tissue wall that is formed at least partially between the first area and the second area.

Example 25: The method of any example disclosed herein, in particular example 24, further comprising advancing a first suture fastener over the one or more first suture tails, locking the first suture fastener in place against a proximal side of the patch, advancing a second suture fastener over the one or more second suture tails, and locking the second suture fastener in place against the proximal side of the patch.

Example 26: The method of any example disclosed herein, in particular example 24, further comprising advancing a suture fastener over the one or more first suture tails and the one or more second suture tails on a proximal side of the patch, and locking the suture fastener in place against a proximal side of the patch.

Example 27: A repair device comprising a handle, an elongate shaft emanating from the handle, a plurality of tissue anchors disposed within the elongate shaft, a plurality of suture-form tissue anchors, each of the plurality of tissue anchors having coupled thereto a respective one of a plurality of sets of suture tails, and an occluder form slidably coupled to the plurality of sets of suture tails within the elongate shaft.

Example 28: The repair device of any example disclosed herein, in particular example 27, further comprising one or more needles disposed within the elongate shaft, each of the plurality of tissue anchors being disposed on a distal portion of one of the one or more needles.

Example 29: The repair device of any example disclosed herein, in particular example 27, wherein the occluder form comprises a patch.

Example 30: The repair device of any example disclosed herein, in particular example 27, wherein the plurality of sets of suture tails are threaded through the occluder form.

Example 31: The repair device of any example disclosed herein, in particular example 27, further comprising a pusher disposed at least partially within the elongate shaft and configured to advance the occluder form distally over the plurality of sets of suture tails.

Example 32: The repair device of any example disclosed herein, in particular example 27, wherein each of the plurality of sets of suture tails consists of a single suture tail.

Example 33: The repair device of any example disclosed herein, in particular example 27, wherein each of the plurality of sets of suture tails comprises two suture tails.

Example 34: A defect repair assembly comprising a plurality of tissue anchors, each of the plurality of tissue anchors having one of a plurality of sets of suture tails emanating therefrom, an occluder patch having the plurality of sets of suture tails slidably coupled thereto, the plurality of tissue anchors being on a first side of the occluder patch, and one or more suture-locking fasteners coupled to at least some of the plurality of sets of suture tails on a second side of the occluder patch opposite the first side.

Example 35: The defect repair assembly of any example disclosed herein, in particular example 34, wherein the plurality of tissue anchors and the occluder patch are disposed within a shaft of a repair device.

Example 36: The defect repair assembly of any example disclosed herein, in particular example 34, wherein the plurality of tissue anchors are deployed on a first side of a tissue wall, and the occluder patch is deployed on a second side of the tissue wall.

Example 37: The defect repair assembly of any example disclosed herein, in particular example 34, wherein the one or more suture-locking fasteners comprises a separate suture-locking fastener coupled to each of the plurality of sets of suture tails.

Example 38: The defect repair assembly of any example disclosed herein, in particular example 34, wherein the one or more suture-locking fasteners consists of a single separate suture-locking fastener coupled the plurality of sets of suture tails.

Methods and structures disclosed herein for treating a patient also encompass analogous methods and structures performed on or placed on a simulated patient, which is useful, for example, for training; for demonstration; for procedure and/or device development; and the like. The simulated patient can be physical, virtual, or a combination of physical and virtual. A simulation can include a simulation of all or a portion of a patient, for example, an entire body, a portion of a body (e.g., thorax), a system (e.g., cardiovascular system), an organ (e.g., heart), or any combination thereof. Physical elements can be natural, including human or animal cadavers, or portions thereof; synthetic; or any combination of natural and synthetic. Virtual elements can be entirely in silica, or overlaid on one or more of the physical components. Virtual elements can be presented on any combination of screens, headsets, holographically, projected, loud speakers, headphones, pressure transducers, temperature transducers, or using any combination of suitable technologies.

Any of the various systems, devices, apparatuses, etc. in this disclosure can be sterilized (e.g., with heat, radiation, ethylene oxide, hydrogen peroxide, etc.) to ensure they are safe for use with patients, and the methods herein can comprise sterilization of the associated system, device, apparatus, etc. (e.g., with heat, radiation, ethylene oxide, hydrogen peroxide, etc.).

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the inventions herein disclosed and claimed below should not be limited by the particular examples described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of repairing a septal defect, the method comprising:

inserting a rigid lumen of a hemostatic introducer through a chest wall portion that is over a left atrium of a heart of a patient;

advancing a rigid elongate shaft through the rigid lumen of the hemostatic introducer, through an outer atrial wall of the left atrium, and into the left atrium;

contacting an atrial septum of the heart with a distal end of the rigid elongate shaft, thereby forming a straight working lumen from outside the chest wall portion and spanning laterally across the left atrium directly to the atrial septum;

deploying a plurality of tissue anchors from the rigid elongate shaft in tissue of the atrial septum; and cinching suture tails associated with the plurality of tissue anchors to at least partially close a defect in the atrial septum.

2. The method of claim 1, further comprising locking the suture tails in a cinched configuration.

3. The method of claim 2, further comprising advancing a suture fastener distally over the suture tails, wherein said locking the suture tails involves locking the suture fastener.

4. The method of claim 1, further comprising cutting-off proximal portions of the suture tails.

5. The method of claim 1, wherein the plurality of tissue anchors comprises three or more tissue anchors.

6. The method of claim 1, wherein the plurality of tissue anchors comprise suture-form knot anchors.

7. The method of claim 6, wherein each of the suture tails is integrated with a respective one of the suture-form knot anchors.

8. The method of claim 1, wherein said advancing the rigid elongate shaft into the left atrium is via a minimally-invasive access, between adjacent ribs.

9. The method of claim 1 wherein;

a pledget is disposed about the suture tails and advanced distally along the suture tails toward the septal defect using a pusher disposed within the elongate shaft; and the pledget is disposed within the elongate shaft and is advanced distally along the suture tails toward the septal defect after deployment of the plurality of tissue anchors.

10. The method of claim 1, wherein the introducer comprises one or more hemostasis valves.

11. The method of claim 1, wherein said deploying the plurality of tissue anchors involves:

puncturing the atrial septum with one or more needles deployed from the elongate shaft; and pushing the plurality of tissue anchors off the one or more needles.

12. The method of claim 11, wherein:

the one or more needles comprises a first needle and a second needle;

each of the first and second needles, prior to said pushing, has winds of suture of one of the plurality of tissue anchors disposed about a distal portion thereof; and said puncturing the atrial septum involves simultaneously deploying the first and second needles from the elongate shaft.

13. The method of claim 1, wherein said deploying the plurality of tissue anchors involves deploying a tissue anchor within a thickness of the atrial septum.

14. The method of claim 13, further comprising performing a short-throw needle puncture into the atrial septum prior to deploying the tissue anchor.

15. The method of claim 1, further comprising withdrawing the rigid elongate shaft away from the atrial septum, thereby exposing the suture tails in the left atrium.

16. A method of repairing a septal defect, the method comprising:

advancing a rigid elongate shaft through a chest wall and through an outer atrial wall into a left atrium of a heart, the rigid elongate shaft housing a plurality of needles arranged in a parallel relationship;

positioning a distal end of the rigid elongate shaft at a target position at least partially over a septal defect in an atrial septum such that the distal end overlies at least a portion of a periphery of the septal defect;

deploying, from the distal end of the rigid elongate shaft while maintaining the distal end at the target position, the plurality of needles through septal tissue at a plurality of spaced locations around the periphery of the septal defect, the plurality of needles being arranged in a parallel relationship within the elongate shaft;

sliding a plurality of suture-form tissue anchors off respective ones of the plurality of needles while the distal end of the elongate shaft remains at the target position;

withdrawing the plurality of needles while leaving the plurality of tissue anchors implanted in the septal tissue; and cinching suture tails associated with the plurality of tissue anchors to approximate edges of the septal defect.

17. The method of claim 16, wherein said deploying the plurality of needles in performed simultaneously.

18. The method of claim 16, wherein said deploying the plurality of needles in performed sequentially.

19. A method of repairing a septal defect, the method comprising:

advancing a rigid elongate shaft through a chest wall, through an outer atrial wall into a left atrium of a heart of a patient's body, and into contact with an atrial septum;

deploying first and second tissue anchors in septal tissue of the atrial septum adjacent a septal defect, the first tissue anchor having a first suture tail and the second tissue anchor having a second suture tail, the first and second suture tails passing through the atrial septum;

threading the first and second suture tails through one or more coils of a knot portion of a locking suture, the one or more coils defining a passage through the knot through which the suture tails pass;

advancing the knot portion of the locking suture distally along the first and second suture tails using a knot holder shaft disposed within the rigid elongate shaft while the knot portion is in a delivery configuration in which the knot portion is slidable relative to the first and second suture tails;

approximating the tissue anchors toward one another by distal advancement of the knot portion; and after achieving a desired approximation of the septal defect, transitioning the knot portion from the delivery configuration to a deployed configuration by proximally pulling a tether line running proximally from the knot portion to constrict the coils around the first and second suture tails to inhibit relative motion between the knot portion and the first and second suture tails.

20. The method of claim 19, wherein:

the knot holder shaft includes a side aperture;

the tether line runs proximally through a distal axial opening of the knot holder shaft and out of the side aperture; and proximally pulling the tether line is performed from outside of the patient's body.

* * * * *